(12) United States Patent
Crum et al.

(10) Patent No.: US 9,198,635 B2
(45) Date of Patent: Dec. 1, 2015

(54) METHOD AND APPARATUS FOR PREPARING ORGANS AND TISSUES FOR LAPAROSCOPIC SURGERY

(75) Inventors: Lawrence A. Crum, Bellevue, WA (US); Peter J. Kaczkowski, Seattle, WA (US); Stuart B. Mitchell, Lake Forest Park, WA (US); Michael R. Bailey, Seattle, WA (US)

(73) Assignee: University of Washington, Seattle, WA (US)

( * ) Notice: Subject to any disclaimer, the term of this patent is extended or adjusted under 35 U.S.C. 154(b) by 2325 days.

(21) Appl. No.: 11/464,118

(22) Filed: Aug. 11, 2006

(65) Prior Publication Data

US 2007/0004984 A1 Jan. 4, 2007

Related U.S. Application Data

(60) Continuation-in-part of application No. 10/171,149, filed on Jun. 13, 2002, now abandoned, which is a continuation of application No. 09/390,032, filed on Sep. 3, 1999, now Pat. No. 6,432,067, which is a (Continued)

(51) Int. Cl.
*A61B 8/00* (2006.01)
*A61B 8/12* (2006.01)
(Continued)

(52) U.S. Cl.
CPC ..... *A61B 8/12* (2013.01); *A61B 8/06* (2013.01); *A61F 7/02* (2013.01); *A61B 8/13* (2013.01);
(Continued)

(58) Field of Classification Search
USPC .......................... 600/371, 439, 454; 601/1, 2
See application file for complete search history.

(56) References Cited

U.S. PATENT DOCUMENTS

| 385,256 A | 6/1888 | Eggers |
| 2,992,553 A | 7/1961 | Joy .................................. 73/644 |

(Continued)

FOREIGN PATENT DOCUMENTS

| DE | 04230415 A1 | 3/1994 | ............... A61B 8/00 |
| EP | 0 420 758 | 4/1991 | ............... A61B 8/00 |

(Continued)

OTHER PUBLICATIONS

Amenta et al., "A New Voronoi-Based Surface Reconstruction Algorithm." *Computer Graphics*: 7pp, 1998.

(Continued)

*Primary Examiner* — Unsu Jung
*Assistant Examiner* — Joseph M Santos Rodriguez
(74) *Attorney, Agent, or Firm* — Kilpatrick Townsend and Stockton LLP

(57) ABSTRACT

High intensity ultrasound (HIU) is used to facilitate surgical procedures, such as a laparoscopic partial nephrectomy, with minimal bleeding. An apparatus is configured to emit HIU from one or more transducers that are attached to a minimally invasive surgical instrument. Such a tool preferably can provide sufficient clamping pressure to collapse blood vessels' walls, so that they will be sealed by the application of the HIU, and by the resulting thermal ablation and tissue cauterization. Such an instrument can provide feedback to the user that the lesion is completely transmural and that blood flow to the region distal of the line of thermal ablation has ceased. Similar instruments having opposed arms can be configured for use in conventional surgical applications as well. Instruments can be implemented with transducers on only one arm, and an ultrasound reflective material disposed on the other arm.

53 Claims, 9 Drawing Sheets

Related U.S. Application Data division of application No. 08/961,972, filed on Oct. 31, 1997, now Pat. No. 6,007,499.

(60) Provisional application No. 60/707,641, filed on Aug. 12, 2005.

(51) Int. Cl.
*A61B 8/06* (2006.01)
*A61F 7/02* (2006.01)
*A61B 8/13* (2006.01)
*A61B 17/32* (2006.01)
*A61B 17/00* (2006.01)

(52) U.S. Cl.
CPC ....... *A61B 8/4272* (2013.01); *A61B 17/320092* (2013.01); *A61B 2017/00243* (2013.01); *A61B 2017/00575* (2013.01)

(56) References Cited

U.S. PATENT DOCUMENTS

| | | | |
|---|---|---|---|
| 4,059,098 A | 11/1977 | Murdock | 128/2 |
| 4,452,081 A * | 6/1984 | Seppi | 73/597 |
| 4,484,569 A | 11/1984 | Driller et al. | 128/60 |
| 4,545,386 A | 10/1985 | Hetz et al. | 600/462 |
| 4,577,506 A * | 3/1986 | Poole et al. | 73/633 |
| 4,601,296 A | 7/1986 | Yerushalmi | 607/156 |
| 4,688,578 A | 8/1987 | Takano et al. | 128/660 |
| 4,708,836 A | 11/1987 | Gain et al. | 264/40.1 |
| 4,773,865 A | 9/1988 | Baldwin | 434/268 |
| 4,976,267 A * | 12/1990 | Jeffcott et al. | 600/437 |
| RE33,590 E | 5/1991 | Dory | 600/439 |
| 5,039,774 A | 8/1991 | Shikinami et al. | 528/60 |
| 5,065,742 A | 11/1991 | Belikan et al. | 128/24 |
| 5,080,101 A | 1/1992 | Dory | 128/660.03 |
| 5,080,102 A | 1/1992 | Dory | 128/660.03 |
| 5,088,498 A | 2/1992 | Beach et al. | 600/453 |
| 5,150,712 A | 9/1992 | Dory | 128/660.03 |
| 5,170,790 A | 12/1992 | Lacoste et al. | 600/437 |
| 5,178,148 A | 1/1993 | Lacoste et al. | 600/439 |
| 5,183,046 A | 2/1993 | Beach et al. | 600/453 |
| 5,194,291 A | 3/1993 | D'Aoust et al. | 148/276 |
| 5,209,221 A * | 5/1993 | Riedlinger | 601/2 |
| 5,215,680 A | 6/1993 | D'Arrigo | 516/11 |
| 5,219,401 A | 6/1993 | Cathignol et al. | 128/660.03 |
| 5,230,334 A | 7/1993 | Klopotek | |
| 5,289,820 A | 3/1994 | Beach et al. | 600/443 |
| 5,311,869 A | 5/1994 | Okazaki | 128/660.03 |
| 5,322,055 A * | 6/1994 | Davison et al. | 601/2 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/660.03 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,520,188 A | 5/1996 | Hennige et al. | 128/662.03 |
| 5,522,878 A | 6/1996 | Montecalvo et al. | 607/152 |
| 5,526,815 A | 6/1996 | Granz et al. | 128/660.03 |
| 5,534,232 A | 7/1996 | Denes et al. | 422/186.26 |
| 5,536,489 A | 7/1996 | Lohrmann et al. | 424/9.52 |
| 5,558,092 A | 9/1996 | Unger et al. | 128/660.03 |
| 5,573,497 A | 11/1996 | Chapelon et al. | 601/2 |
| 5,609,485 A | 3/1997 | Bergman et al. | 434/262 |
| 5,638,823 A | 6/1997 | Akay et al. | 600/528 |
| 5,657,760 A | 8/1997 | Ying et al. | |
| 5,666,954 A | 9/1997 | Chapelon et al. | 600/439 |
| 5,716,374 A | 2/1998 | Francese et al. | 606/207 |
| 5,720,286 A | 2/1998 | Chapelon et al. | 600/439 |
| 5,720,287 A | 2/1998 | Chapelon et al. | 600/439 |
| 5,726,066 A | 3/1998 | Choi | 438/3 |
| 5,755,228 A | 5/1998 | Wilson et al. | 128/660.06 |
| 5,762,066 A | 6/1998 | Law et al. | 600/439 |
| 5,769,790 A | 6/1998 | Watkins et al. | 600/439 |
| 5,807,285 A | 9/1998 | Vaitekunas | 601/2 |
| 5,810,007 A | 9/1998 | Holupka et al. | 600/439 |
| 5,817,021 A | 10/1998 | Reichenberger | 600/439 |
| 5,823,962 A | 10/1998 | Schaetzle et al. | 600/439 |
| 5,824,277 A | 10/1998 | Campos | 423/242.1 |
| 5,827,204 A | 10/1998 | Grandia et al. | 601/2 |
| 5,833,647 A | 11/1998 | Edwards | 604/22 |
| 5,840,028 A | 11/1998 | Chubachi et al. | 600/437 |
| 5,846,517 A | 12/1998 | Unger | 424/9.52 |
| 5,853,752 A | 12/1998 | Unger et al. | 424/450 |
| 5,873,828 A | 2/1999 | Fujio et al. | 600/439 |
| 5,879,314 A | 3/1999 | Peterson et al. | 601/2 |
| 5,882,302 A | 3/1999 | Driscoll, Jr. et al. | 600/371 |
| 5,895,356 A | 4/1999 | Andrus et al. | 600/439 |
| 5,897,495 A | 4/1999 | Aida et al. | 600/411 |
| 5,906,580 A | 5/1999 | Kline-Schoder et al. | 600/459 |
| 5,919,139 A | 7/1999 | Lin | 600/443 |
| 5,922,945 A | 7/1999 | Allmaras et al. | 73/52 |
| 5,931,786 A | 8/1999 | Whitmore et al. | 600/459 |
| 5,935,339 A | 8/1999 | Henderson et al. | 134/1 |
| 5,951,476 A | 9/1999 | Beach | 600/437 |
| 5,976,092 A | 11/1999 | Chinn | 600/459 |
| 5,993,389 A | 11/1999 | Driscoll, Jr. et al. | 600/371 |
| 5,997,481 A | 12/1999 | Adams et al. | 600/459 |
| 6,007,499 A | 12/1999 | Martin et al. | 601/3 |
| 6,036,650 A | 3/2000 | Wu et al. | 600/462 |
| 6,039,694 A * | 3/2000 | Larson et al. | 600/459 |
| 6,050,943 A | 4/2000 | Slayton et al. | 600/439 |
| 6,067,371 A | 5/2000 | Gouge et al. | 382/128 |
| 6,071,239 A | 6/2000 | Cribbs et al. | 600/439 |
| 6,083,159 A * | 7/2000 | Driscoll et al. | 600/371 |
| 6,099,539 A * | 8/2000 | Howell et al. | 606/151 |
| 6,128,522 A | 10/2000 | Acker et al. | 600/411 |
| 6,179,831 B1 | 1/2001 | Bliweis | 606/21 |
| 6,200,539 B1 | 3/2001 | Sherman et al. | 422/186.04 |
| 6,221,015 B1 | 4/2001 | Yock | 600/439 |
| 6,267,734 B1 | 7/2001 | Ishibashi | 601/2 |
| 6,406,759 B1 | 6/2002 | Roth | 427/562 |
| 6,409,720 B1 | 6/2002 | Hissong et al. | 606/27 |
| 6,425,867 B1 | 7/2002 | Vaezy | 600/439 |
| 6,443,894 B1 | 9/2002 | Sumanaweera et al. | 600/443 |
| 6,488,639 B1 | 12/2002 | Ribault et al. | 601/2 |
| 6,491,672 B2 | 12/2002 | Slepian et al. | 604/267 |
| 6,548,047 B1 | 4/2003 | Unger | 424/9.51 |
| 6,551,576 B1 | 4/2003 | Unger et al. | 424/9.52 |
| 6,584,360 B2 | 6/2003 | Francischelli et al. | 607/98 |
| 6,595,934 B1 | 7/2003 | Hissong et al. | 601/3 |
| 6,599,256 B1 | 7/2003 | Acker et al. | 601/2 |
| 6,626,855 B1 | 9/2003 | Weng et al. | 601/3 |
| 6,633,658 B1 | 10/2003 | Dabney et al. | 382/128 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,692,450 B1 * | 2/2004 | Coleman | 601/3 |
| 6,706,892 B1 | 3/2004 | Ezrin et al. | 548/548 |
| 6,709,407 B2 | 3/2004 | Fatemi | 600/559 |
| 6,716,184 B2 | 4/2004 | Vaezy et al. | 601/3 |
| 6,719,694 B2 | 4/2004 | Weng et al. | 600/439 |
| 6,719,699 B2 | 4/2004 | Smith | 600/459 |
| 6,726,627 B1 | 4/2004 | Lizzi et al. | 600/439 |
| 6,764,488 B1 | 7/2004 | Burbank et al. | 606/51 |
| 6,846,291 B2 | 1/2005 | Smith et al. | 600/459 |
| 6,875,176 B2 | 4/2005 | Mourad et al. | 600/442 |
| 6,875,420 B1 | 4/2005 | Quay | 424/9.52 |
| 6,905,498 B2 | 6/2005 | Hooven | 606/50 |
| 6,932,771 B2 | 8/2005 | Whitmore et al. | 607/105 |
| 6,955,648 B2 | 10/2005 | Mozayeni et al. | 600/454 |
| 7,052,463 B2 | 5/2006 | Peszynski et al. | 600/459 |
| 7,149,564 B2 | 12/2006 | Vining et al. | 600/425 |
| 7,260,250 B2 | 8/2007 | Summers et al. | 382/128 |
| 7,470,241 B2 | 12/2008 | Weng et al. | 601/3 |
| 7,628,764 B2 | 12/2009 | Duarte et al. | 601/2 |
| 2002/0169394 A1* | 11/2002 | Eppstein et al. | 600/573 |
| 2002/0193681 A1 | 12/2002 | Vitek et al. | 600/411 |
| 2002/0193831 A1 | 12/2002 | Smith, III | 607/5 |
| 2003/0013970 A1* | 1/2003 | Makin | 600/459 |
| 2003/0018255 A1 | 1/2003 | Martin et al. | 600/3 |
| 2003/0028111 A1* | 2/2003 | Vaezy et al. | 600/439 |
| 2003/0069569 A1 | 4/2003 | Burdette et al. | 606/27 |
| 2003/0120268 A1* | 6/2003 | Bertolero et al. | 606/32 |

(56) References Cited

U.S. PATENT DOCUMENTS

| | | | |
|---|---|---|---|
| 2003/0125623 A1 | 7/2003 | Kelly et al. | 600/437 |
| 2003/0195420 A1 | 10/2003 | Mendlein et al. | 600/459 |
| 2003/0208101 A1 | 11/2003 | Cecchi | 600/466 |
| 2004/0002654 A1 | 1/2004 | Davidson et al. | 600/454 |
| 2004/0019278 A1 | 1/2004 | Abend | 600/545 |
| 2004/0059220 A1 | 3/2004 | Mourad et al. | 600/442 |
| 2004/0078034 A1 | 4/2004 | Acker et al. | 606/27 |
| 2004/0097805 A1 | 5/2004 | Verard et al. | 600/428 |
| 2004/0097840 A1 | 5/2004 | Holmer | 601/2 |
| 2004/0122493 A1 | 6/2004 | Ishibashi et al. | 600/437 |
| 2004/0143186 A1 | 7/2004 | Anisimov et al. | 600/437 |
| 2004/0153126 A1 | 8/2004 | Okai | 607/1 |
| 2004/0181178 A1 | 9/2004 | Aldrich et al. | 601/3 |
| 2004/0234453 A1 | 11/2004 | Smith | 424/9.5 |
| 2004/0254620 A1 | 12/2004 | Lacoste et al. | 607/96 |
| 2005/0065436 A1 | 3/2005 | Ho et al. | 600/431 |
| 2005/0182319 A1 | 8/2005 | Glossop | 600/424 |
| 2005/0240102 A1 | 10/2005 | Rachlin et al. | 600/437 |
| 2006/0184069 A1 | 8/2006 | Vaitekunas | 601/2 |
| 2008/0045864 A1 | 2/2008 | Candy et al. | 601/2 |
| 2008/0045865 A1 | 2/2008 | Kislev | 601/3 |
| 2008/0200815 A1 | 8/2008 | Van Der Steen et al. | 600/467 |
| 2008/0319375 A1 | 12/2008 | Hardy | 604/22 |

FOREIGN PATENT DOCUMENTS

| | | | |
|---|---|---|---|
| EP | 01265223 B1 | 11/2002 | G10K 11/35 |
| FR | WO 00/72919 | 12/2000 | A61N 7/02 |
| JP | H09-103434 | 4/1997 | A61B 17/36 |
| JP | 2002-500939 | 1/2002 | A61B 18/00 |
| JP | 2004-113789 | 4/2004 | A61B 8/00 |
| WO | WO 97/31364 | 8/1997 | G10K 11/02 |
| WO | WO 02/069805 | 9/2002 | A61B 8/06 |

OTHER PUBLICATIONS

American Red Cross., "Blood 101." 4pp., Dec. 11, 2007.
Anand et al., "Monitoring formation of high intensity focused ultrasound (HIFU) induced lesions using backscattered ultrasound." *Acoustical Society of America*; Mar. 10, 2004.
Aurenhammer, F. "Voronoi diagrams—A Survey of a Fundamental Geometric Data Structure." *ACM Computing Surveys*, vol. 23, No. 3: 345-405, Sep. 1991.
Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.
Beard et al., "An Annular Focus Ultrasonic Lens for Local Hyperthermia Treatment of Small Tumors." *Ultrasound in Medicine & Biology*; vol. 8, No. 2: 177-184, 1982.
Bokarewa et al., "Tissue factor as a proinflammatory agent." *Arthritis Research*, vol. 4: 190-195, Jan. 10, 2002.
Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.
Buller et al., "Accurate Three-dimensional Wall Thickness Measurement From Multi-Slice Short-Axis MR Imaging." *Computers in Cardiology*, 245-248, 1995.
Chao et al., "Aspheric lens design." *Ultrasonics Symposium, 2000 IEEE*, vol. 2: Abstract Only, Oct. 2000.
Cheliue et al., "Fabrication of Medical Models From Scan Data via Rapid Prototyping Techniques." 9 pp., Feb. 7, 2007.
Chong et al., "Tissue Factor and Thrombin Mediate Myocardial Ischemia-Reperfusion Injury." *The Society of Thoracic Surgeons*, vol. 75: S649-655, 2003.
Dempsey et al., "Thickness of Carotid Artery Atherosclerotic Plaque and Ischemic Risk." *Neurosurgery*, vol. 27, No. 3: 343-348, 1990.
Ebbini et al., "Image-guided noninvasive surgery with ultrasound phased arrays." *SPIE*, vol. 3249: 230-239, Apr. 2, 1998.
Edelsbrunner, Herbert. "Geometry and Topology for Mesh Generation." Cambridge University Press: 68pp, 2001.
Ewert et al., "Anti-myeloperoxidase antibodies stimulate neutrophils to damage human endothelial cells." *Kidney International*, vol. 41: 375-383, 1992.
Ganapathy et al., "A New General Triangulation Method for Planar Contours." *Computer Graphics* vol. 16, No. 3:69-75, 1982.
Gray, Henry. "The Skull." *Anatomy of the Human Body*: 7pp., 1918.
Hadimioglu et al., "High-Efficiency Fresnel Acoustic Lenses." *Ultrasonics Symposium 1993 IEEE*: 579-582, 1993.
Han et al., "A Fast Minimal Path Active Contour Model." IEEE Transactions on Image Processing, vol. 10, No. 6: 865-873, Jun. 2001.
Hubka et al., "Three-dimensional echocardiographic measurement of left ventricular wall thickness: In vitro and in vivo validation." *Journal of the American Society of Echocardiography*, vol. 15, No. 2: 129-135, 2002.
Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.
Iannuzzi et al., "Ultrasonographic Correlates of Carotid Atherosclerosis in Transient Ischemic Attack and Stroke." *Stroke*, ProQuest Medical Library, vol. 26, No. 4: 614-619, 1995.
Idell et al., "Fibrin Turnover in Lung Inflammation and Neoplasia." *American Journal of Respiratory and Critical Care Medicine*, vol. 163: 578-584, 2001.
Kang et al., "Analysis of the Measurement Precision of Arterial Lumen and Wall Areas Using High-Resolution MRI." *Magnetic Resonance in Medicine*, vol. 44: 968-972, 2000.
Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.
Meyers, D. "Multiresolution tiling." *Computer Graphics*, No. 5: 325-340, 1994.
Miller et al., "Diagnostic ultrasound activation of contrast agent gas bodies induces capillary rupture in mice." *PNAS*, vol. 97, No. 18: 10179-10184, 2000.
O'Leary et al., "Carotid-artery Intima and Media Thickness as a Risk Factor for Myocardial Infarction and Stroke in Older Adults." Cardiovascular Health Study Collaborative Research Group. *New England Journal of Medicine*, vol. 340, No. 1: 14-22, Jan. 7, 1999.
Pignoli et al., "Intimal plus medial thickness of the arterial wall: a direct measurement with ultrasound imaging." *Circulation*, vol. 74, No. 6:1399-1406, Dec. 1986.
Rosen et al., "Vascular Occlusive Diseases." 37pp., revised 2002.
Schulte-Altedorneburg et al., "Accuracy of In Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.
Tardy et al., "In Vivo Ultrasound Imaging of Thrombi Using a Target-specific Contrast Agent." *Academy of Radiology*, vol. 9, Suppl. 2: S294-S296, 2002.
Vaezy et al., "Hemostasis using high intensity focused ultrasound." *European Journal of Ultrasound*, vol. 9: 79-87, 1999.
Vaezy et al., "Intra-operative acoustic hemostasis of liver: production of a homogenate for effective treatment." *Ultrasonics*, vol. 43: 265-269, 2005.
Von Land et al., "Development of an Improved Centerline Wall Motion Model." *IEEE*: 687-690, 1991.
Williamson et al., "Color Doppler Ultrasound Imaging of the Eye and Orbit." *Survey of Ophthamology*, vol. 40, No. 4: 255-267, 1996.
Yu et al., "A microbubble agent improves the therapeutic efficiency of high intensity focused ultrasound: a rabbit kidney study." *Urological Research*, PubMed: Abstract, 2004.
N.a., "Cavitation." Ultrasound TIP—U.S. Database: Dec. 12, 2007.
Aaslid et al., "Noninvasive transcranial Doppler ultrasound recording of flow velocity in basal cerebral arteries." *Journal of Neurosurgery*, vol. 57: 769-774, 1982.
Campbell et al. "Pulsatile Echo-encephalography." *Acta Neurologica Scandinavica Supplementum 45*, vol. 46: 1-57, 1970.
Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.

(56) References Cited

OTHER PUBLICATIONS

Gao et al., "Imaging of the Elastic Properties of Tissue—A Review." *Ultrasound in Medicine & Biology*, vol. 22, No. 8: 959-977, 1996.
Klingelhöfer et al., "Chapter 4: Functional Ultrasonographic Imaging" In Babikian VL, Wechsler LR, eds. *Transcranial Doppler Ultrasonography*. Woburn, MA: Butterworth-Heinemann, 49-66, 1999.
Markwalder et al., "Dependency of Blood Flow Velocity in the Middle Cerebral Artery on End-Tidal Carbon Dioxide Partial Pressure—A Transcranial Ultrasound Doppler Study." *Journal of Cerebral Blood Flow and Metabolism*, vol. 4, No. 3: 368-372, 1984.
Accord, Ray E. "The Issue of Transmurality in Surgical Ablation for Atrial Fibrillation" Cardiothoracic Surgery Network, Aug. 8, 2005.
Anand, Ajay et al. "Using the ATL 1000 to Collect Domodulated RF Data for Monitoring HIFU Lesion Formation." Center for Industrial and Medical Ultrasound, University of Washington. Abstract. 11pp.
Bauer, A., Solbiati, L., Weissman, N. "Ultrasound Imaging with SonoVue: Low Mechanical Index Real-time Imaging." *Acad Radiol* 2002, 9(suppl 2): S282-S284.
Brayman, A., Lizotte, L., Miller, M. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305-1320, 1999.
Chen, Wen-Shiang et al. "A comparison of the fragmentation thresholds and inertial cavitation doses of different ultrasound contrast agents." J. Acoust. Soc. Am. 113 (1) Jan. 2003, pp. 643-651.
Chen, Wen-Shiang et al. "Inertial Cavitation Dose and Hemolysis Produced in Vitro with or Without Optison." Ultrasound in Med. & Biol., vol. 29, No. 5, pp. 725-737, 2003.
Dayton, P. et al. "The magnitude of radiation force on ultrasound contrast agents." J. Acoust. Soc. Am. 112 (5) Pt. 1, Nov. 2002, pp. 2183-2192.
Everbach, C., and Francis, C. "Cavitational Mechanisms in Ultrasound/Accelerated Thrombolysis at 1 MHz." Ultrasound in Med. & Biol., vol. 26, No. 7, pp. 1153-1160, 2000.
Guzman, H. et al. "Ultrasound-Mediated Disruption of Cell Membranes. I. Quantification of Molecular Uptake and Cell Viability." J. Acoust. Soc. Am. 110 (1), Jul. 2001, pp. 588-595.
Guzman, H. et al. "Ultrasound-Mediated Disruption of Cell Membranes. II. Heterogeneous Effects on Cells." J. Acoust. Soc. Am. 110 (1), Jul. 2001, pp. 597-606.
Hatangadi, R. "A Novel Dual Axis Multiplanar Transesophageal Ultrasound Probe for Three-Dimensional Echocardiograph." University of Washington Department of Science and Engineering. Abstract. vol. 55-11B. 4960pp. 1994.
Holt, G., Roy, R., Edson, P., Yang, X. "Bubbles and Hifu.: the Good, the Bad and the Ugly." Boston University Department of Aerospace and Mechanical Engineering. Boston, MA. 02215: 120-131.
Hynynen, K. et al. "Potential Adverse Effects of High-Intensity Focused Ultrasound Exposure on Blood Vessels in Vivo." Ultrasound in Med. & Biol., vol. 22, No. 2, pp. 193-201, 1996.
Indman, P. "Alternatives in Gynecology." Hysteroscopy © 2000 OBGYN.net <http://www.gynalternatives.com/hsc.html>.
Kaczkowski, P., Vaezy, S., Martin, R., Crum, L. "Development of a High Intensity Focused Ultrasound System for image-guided ultrasonic surgery." Ultrasound for Surgery 2001. <http://cimu.apl.washington.edu/hifusurgerysystem.html>.
Klibanov, A., Rasche, P., Hughes, M., Wojdyla, J., Galen, K., Wiblee, J., Brandenburger, G. "Detection of Individual Microbubbles of an Ultrasound Contrast Agent: Fundamental and Pulse Inversion Imaging." *Acad Radiol* 2002, 9 (suppl 2): S279-S281.

Kudo, N., Miyaoka, T., Okada, K., Yamamoto, K. "Study on Mechanism of Cell Damage Caused by Microbubbles Exposed to Ultrasound." Graduate School of Engineering, Hokkaido University, Japan, Research Institute for Electronic Science, Hokkaido University, 060-0812 Japan.
Miller, M. et al. "A Review of In Vitro Bioeffects of Intertial Ultrasonic Cavitaion From a Mechanistic Perspective." Ultrasound in Med. & Biol., vol. 22, No. 9, pp. 1131-1154, 1996.
Ng, K., Liu, Y. "Therapeutic Ultrasound: Its Application in Drug Delivery." Medicinal Research Reviews, vol. 22, 204-233, 2002.
Ostensen, J., Bendiksen, R. "Characterization and Use of Ultrasound Contrast Agents." *Acad Radiol* 2002 9 (suppl 2): S276-S278.
Owaki, T., Nakano, S., Arimura, K., Aikou, T. "The Ultrasonic Coagulating and Cutting System Injuries Nerve Function." First Department of Surgery, Kagoshima University School of Medicine, Kagoshima, Japan, Endoscopy. 2002. 575-579.
Poliachik, S. et al. "Activation, Aggregation and Adhesion of Platelets Exposed to High-Intensity Focused Ultrasound." Ultrasound in Med. & Biol., vol. 27, No. 11, pp. 1567-1576, 2001.
Poliachik, S. et al. "Effect of High-Intensity Focused Ultrasound on Whole Blood With or Without Microbubble Contrast Agent." Ultrasound in Med. & Biol., vol. 25, No. 6, 1999: 991-998.
Porter, T., Xie, F. "Ultrasound, Microbubbles and Thrombolysis." Progress in Cardiovascular Diseases, vol. 44, No. 2, Oct. 2001, pp. 101-110.
Rivens, I., Rowland, I., Denbow, M., Fisk, N., Harr, G., Leach, M. "Vascular occlusion using focused ultrasound surgery for use in fetal medicine." European Journal of Ultrasound 9. 1999 pp. 89-97.
Rosenschein, U. et al. "Ultrasound Imaging-Guided Noninvasive Ultrasound Thrombolysis-Preclinical Results." © 2000 American Heart Association, Inc. (Circulation. 2000; 102:238-245) <http://www.circulationaha.com.org>.
Rosenschein, U. et al. "Shock-Wave Thrombus Ablation, A New Method for Noninvasive Mechanical Thrombolysis." The American Journal of Cardiology, vol. 70, Issue 15, Nov. 1992, pp. 1358-1361.
Tachibana, K. and S. "The Use of Ultrasound for Drug Delivery." First Department of Anatomy, Fukuoka University School of Medicine, Nanakuma, Japan. Echocardiography. 2001 pp. 323-328.
Tachibana, K. and S. "Albumin Microbubble Echo-Contrast Material as an Enhancer for Ultrasound Accelerated Thrombolysis." (Circulation, 1995; 92: 1148-1150.) © 1995 American Heart Association, Inc.
Vaezy, S. et al. "Acoustic Surgery." Physics World. Aug. 2001. pp. 35-39.
Vaezy, S. et al. "Experimental Investigations and Device Development." First International Workshop on the Application of HIFU in Medicine. (May 10, 2013) 4pp.
Watkin, K., McDonald, M. "Multi-Modal Contrast Agents: A First Step." *Acad Radiol* 2002, 9 (suppl 2): S285-S287.
Watkin, K., McDonald, M. "Schmatic of the Tube, Cross Section Ultrasound Images of the Tube with Different Contrast Media (CM)." *Acad Radiol* 2002 9(suppl 2): S288-S289.
Wickline, S., Hughes, M., Ngo, F., Hall, C., Marsh, J., Brown, P., Allen, J., McLean, M., Scott, M., Fuhrhop, R., Lanza, G. "Blood Contrast Enhancement with a Novel, Non-Gaseous Nanoparticle Contrast Agent." *Acad Radiol* 2002 9(suppl 2): S290-S293.
"Mechanical Bioeffects in the Presence of Gas-Carrier Ultrasound Contrast Agents." J. Ultrasound Med. 19: 120-142, 2000.
Physicians. "Breast Cancer—Insightec: focused ultrasound for non invasive treatment." FAQ <http://www.exablate2000.com/physicians_faq.html>.

* cited by examiner

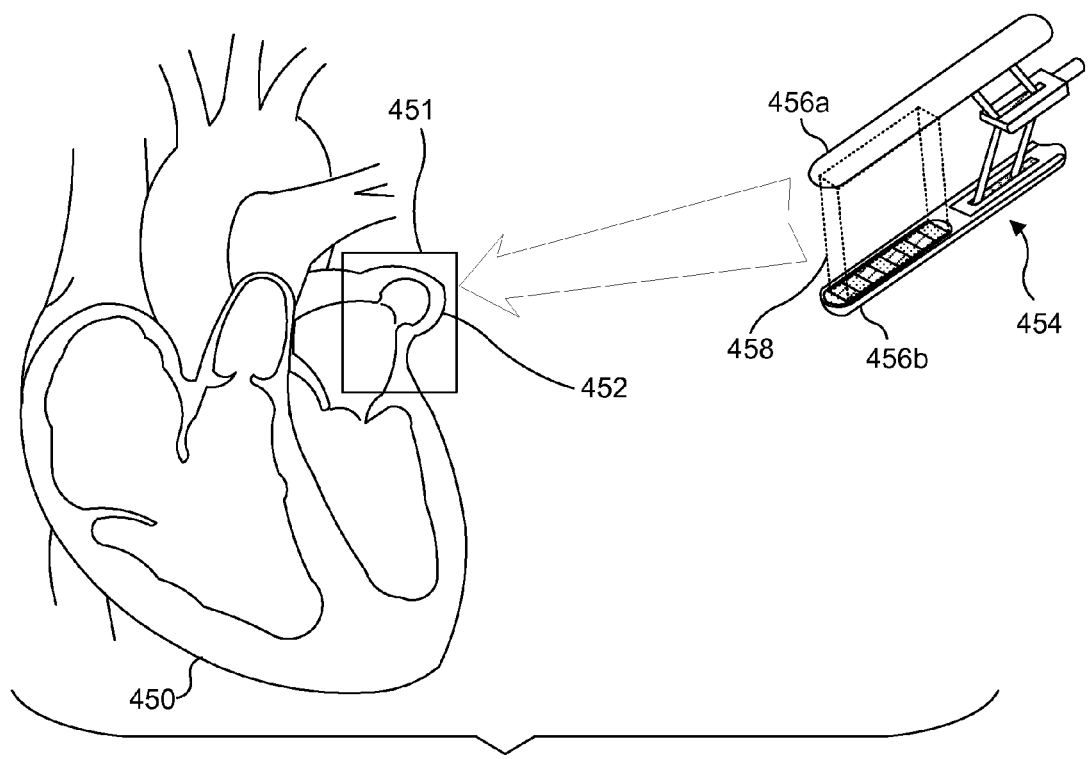
FIG. 10A
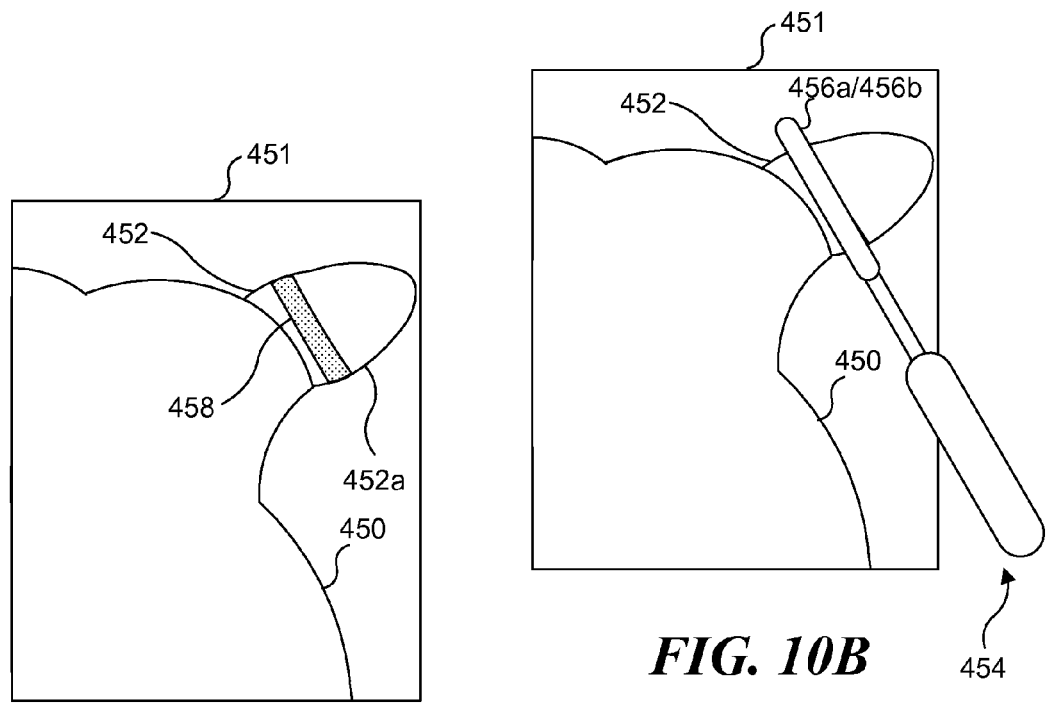
FIG. 10B
FIG. 10C

METHOD AND APPARATUS FOR PREPARING ORGANS AND TISSUES FOR LAPAROSCOPIC SURGERY

RELATED APPLICATIONS

This application is based on a prior provisional application, Ser. No. 60/707,641, filed on Aug. 12, 2005, the benefit of the filing date of which is hereby claimed under 35 U.S.C. §119 (e). This application is also a continuation-in-part of a copending patent application Ser. No. 10/171,149, filed on Jun. 13, 2002, which is a continuation of patent application Ser. No. 09/390,032, filed on Sep. 3, 1999, issued as U.S. Pat. No. 6,432,067 on Aug. 13, 2002, which itself is a divisional application of patent application Ser. No. 08/961,972, filed on Oct. 31, 1997, issued as U.S. Pat. No. 6,007,499 on Dec. 28, 1998, the benefit of the filing dates of which is hereby claimed under 35 U.S.C. §120.

BACKGROUND

There is an ever-increasing effort in health care to develop techniques and approaches that would be less traumatic to the patient. Accordingly, minimally and non-invasive surgical techniques are an active area of interest. For example, techniques such as extracorporeal shock wave lithotripsy have resulted in significantly reduced morbidity in the treatment of renal calculi and have also resulted in greatly improved outcomes to the patient. Emerging technologies, such as image-guided therapies, that involve High Intensity Ultrasound and High Intensity Focused Ultrasound (HIFU) are also becoming increasingly integrated in the armada of tools available to the modem medical clinician.

In one important procedure described in U.S. Pat. No. 6,007,499 (of which the present application is a continuation-in-part), it is demonstrated how the application of HIFU to a section of tissue can introduce a plane of cauterization within the tissue, thus permitting the subsequent resection of the tissue, distal to the plane, without bleeding.

In the U.S. alone, several hundred thousand surgical procedures are performed each year that involve the removal of tissue, or a portion of an organ, because of some pathology involving the tissue. Many of these procedures remove benign or malignant tumors. Although a significant percentage of such tissue and organ removal procedures employ conventional surgical techniques, a major effort has been directed to replacing (as much as possible) conventional surgical techniques with minimally invasive surgical techniques (such as laparoscopic and endoscopic techniques), to reduce morbidity. However, performing such surgery using minimally invasive instruments requires significant training and advanced skills on the part of the operating physician. It would be desirable to provide minimally invasive methods and apparatus that are relatively easier to implement than those currently used.

Almost 400,000 patients were treated for end-stage renal disease (ESRD) in the United States in 2001. The incidence of new beneficiaries of treatment was in excess of 93,000 individuals during the same calendar year, and the mortality attributed to ESRD was well over 76,000 during that year. Many of these individuals are candidates for kidney transplants; however, the demand far exceeds the number of kidneys available for transplant. Thus, clinicians are making efforts to preserve as much of a kidney as possible during renal surgical procedures. Considerable effort has been made to train urologists and surgeons to perform partial nephrectomies during laparoscopic procedures. A laparoscopic partial nephrectomy is a particularly difficult procedure, primarily because it is difficult to prevent and control bleeding during and after the procedure. It is common during a laparoscopic partial nephrectomy to clamp the main renal artery so that tissue removal can be carried out without significant bleeding. If this renal artery is clamped for an excessive time, ischemia can cause long term damage to the remaining tissue.

It would thus be desirable to provide methods and apparatus to facilitate surgical procedures with minimal blood loss, which can be used for laparoscopic partial nephrectomies, as well as for other surgical procedures.

SUMMARY

The disclosure provided herein relates to method and apparatus for using high intensity ultrasound (focused or unfocused) to facilitate the removal of tissue (including organ tissue) or other physiological structures with minimal bleeding. Such tissue removal can occur in the context of minimally invasive procedures, such as a laparoscopic partial nephrectomy, or more conventional surgical practices. The present disclosure encompasses designs for instruments to facilitate the removal of tissue with minimal bleeding, procedures for using such instruments, and techniques for providing an indication to a clinician that target tissue has been sufficiently treated to reduce blood loss to at least an acceptable level.

One aspect disclosed herein is directed to an exemplary apparatus including a pair of opposed arms configured to encompass a mass of tissue (or some other physiological structure) between the opposed arms. At least one arm includes one or more transducers configured to emit high intensity ultrasound generally toward the opposing arm. In some exemplary embodiments, the opposing arm also includes one or more transducers configured to emit high intensity ultrasound. In other exemplary embodiments, the one opposing arm includes a reflector configured to reflect high intensity ultrasound emitted from the other opposing arm back into the mass of tissue (or other physiological structure). Reflectors can be implemented using an air-filled body or a layer of Styrofoam™ (or similar material), or a material having a relatively low acoustic impedance (i.e., an acoustic impedance lower than tissue), or a material having an acoustic impedance substantially different than the acoustic impedance of tissue.

Tissue necrosis (i.e., cauterization/thermal ablation) occurs in the tissue disposed between the opposed arms, and incisions into the necrosed tissue can be made with relatively little blood loss. The apparatus can be moved to generate a plurality of cauterized tissue sites, so that tissue disposed between the plurality of cauterized tissue sites can be removed with relatively little blood loss. In some exemplary embodiments, the apparatus is configured to be coupled to a laparoscopic instrument (or endoscopic instrument, or other minimally invasive instrument) that can be inserted into the body. Embodiments configured to be used with minimally invasive treatments can be disposable (to reduce cost, such embodiments may include fewer transducers than embodiments intended to be reused). In other exemplary embodiments, the apparatus is configured to be used with more invasive surgical techniques (i.e., the apparatus is relatively larger in size than conventional laparoscopic or endoscopic instruments).

In some exemplary embodiments, the opposed arms are configured to provide sufficient clamping pressure to collapse blood vessels walls so that these blood vessels can readily be sealed by the application of high intensity ultrasound, to achieve the resulting thermal ablation and tissue cauterization. In at least one exemplary embodiment, the apparatus provides feedback to the user that the lesion is completely transmural, and that blood flow to the region distal of the line of thermal ablation has ceased. In some exemplary embodiments, the transducers are curved to achieve some degree of focusing, while in other exemplary embodiments, the transducers are not capable of achieving a focused high intensity ultrasound field. A particularly preferred embodiment is configured to achieve a standing wave of high intensity ultrasound between the two opposed arms.

Another aspect disclosed herein is directed to a surgical method with minimal blood loss that uses high intensity ultrasound to induce a plane of cauterization so that the tissue of interest, once transected, does not bleed. Apparatus such as those described above can be used to facilitate such a surgical method. In some embodiments, the surgical method involves minimally invasive methods, whereas in other embodiments, the surgical method involves conventional surgical techniques (i.e., open surgery).

A partial nephrectomy is just one of a number of procedures in which entry into the abdominal gastroenterological cavity is achieved through a small opening to perform a surgical or therapeutic procedure. However, the procedure and apparatus disclosed herein should not be considered to be limited to performing only laparoscopic procedures; indeed, at least one aspect of the disclosure provided herein is directed to an apparatus configured to be used in open surgery, in which tissues to be surgically removed would first be treated with such a device, to isolate the tissue/physiological structure to be removed from the general blood supply. Subsequent removal of the tissue/physiological structure could then be performed without concern for bleeding.

Such a "bloodless surgical" procedure will have broad applications in cases in which there is a limited availability of transfused blood, or in applications in which patients have concerns about blood transfusions.

Another aspect disclosed herein relates to techniques to provide feedback to the user (i.e., clinician) indicating that the target tissue treated with high intensity ultrasound to reduce bleeding has been sufficiently treated to achieve that desired result. In some embodiments, time-of-flight measurements are used to determine a relative temperature of the tissue disposed between the parallel arms of the exemplary apparatus described above, to determine if such tissue has been sufficiently treated to achieve cauterization of tissue. In some exemplary embodiments, Doppler ultrasound is employed to determine if blood flow throughout the tissue disposed between the parallel arms in the apparatus described above has ceased, indicating that the tissue can be incised with minimal blood loss.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 1A and 1B schematically illustrate a high intensity ultrasound transducer positioned to apply the high intensity ultrasound to a mass of tissue;

FIG. 2A schematically illustrates a kidney that has been treated with high intensity ultrasound using the apparatus of FIGS. 1A and 1B;

FIG. 2B schematically illustrates the kidney of FIG. 2A, indicating that after high intensity ultrasound treatment and transection, the treated kidney does not bleed;

FIG. 2C schematically illustrates an end view of the transected kidney of FIG. 2B, indicating that the treated portion of the kidney exhibits complete transmurality, and that all blood vessels in the treated portion of the kidney are substantially occluded;

FIG. 2D schematically illustrates an end view of the transected kidney of FIG. 2B, indicating that the kidney has not been fully treated, such that the treated portion of the kidney does not exhibit complete transmurality, and all blood vessels in the treated portion of the kidney are not substantially occluded;

FIG. 2E schematically illustrates an end view of the transected kidney of FIG. 2B, indicating that the kidney has not been fully treated, such that the treated portion of the kidney exhibits complete transmurality, but not all blood vessels in the treated portion of the kidney are substantially occluded;

FIG. 3A schematically illustrates an exemplary laparoscopic clamp that can be inserted through a trocar and into a body cavity, and once inserted, can expand such that the opposed jaws of the clamp can engage relatively larger structures, such as a kidney;

FIG. 3B schematically illustrates the device of FIG. 3A positioned within an abdominal cavity and being used to clamp tissue;

FIG. 4 is a flowchart schematically illustrating exemplary logical steps of a method for using a medical device substantially similar to that illustrated in FIG. 3A;

FIG. 5A schematically illustrates a plurality of therapy transducers combined with a surgical tool including opposed arms, such as that illustrated in FIG. 3A, such that a generally planar region of tissue disposed between the opposed arms can be thermally treated using high intensity ultrasound to induce tissue necrosis;

FIG. 5B schematically illustrates a technique for determining if a tissue sample has been completely cauterized with high intensity ultrasound, by using the time-of-flight of a number of pulses, spread over the spatial extent of the tissue sample, to determine if the temperature in a particular tissue region has reached the cauterization temperature;

FIG. 5C schematically illustrates a plurality of exemplary therapy transducers combined with a surgical clamp such as that illustrated in FIG. 3A, such that the opposed jaws of the clamp can squeeze the tissue to at least partially occlude blood vessels in the tissue, before a generally planar region of tissue disposed between the opposed jaws of the clamp is thermally treated using high intensity ultrasound to induce tissue necrosis, thereby increasing a likelihood that blood flow in the cauterized tissue will be substantially occluded;

FIG. 6A schematically illustrates opposed arms of a medical device substantially similar to that illustrated in FIG. 3A, wherein each opposed arm comprises at least one ultrasound transducer and an ultrasound absorbent material;

FIG. 6B schematically illustrates opposed arms of a medical device substantially similar to that illustrated in FIG. 3A, wherein a first arm comprises at least one ultrasound transducer and an ultrasound absorbent material, and a second arm comprises an ultrasound reflective material;

FIG. 6C schematically illustrates opposed arms of a medical device substantially similar to that illustrated in FIG. 3A, wherein each opposed arm comprises at least one ultrasound transducer and a membrane configured to facilitate acoustically coupling the at least one ultrasound transducer with tissue disposed between the opposed arms;

FIG. 6D schematically illustrates opposed arms of a medical device substantially similar to that illustrated in FIG. 3A, wherein each opposed arm comprises at least one ultrasound transducer and a fluid conduit configured to provide a coupling fluid/gel to facilitate acoustically coupling the at least one ultrasound transducer with tissue disposed between the opposed arms;

FIG. 6E schematically illustrates a single arm of a medical device substantially similar to that illustrated in FIG. 3A, wherein the arm comprises an ultrasound array including at least one element disposed orthogonally to other elements in the array;

FIG. 6F schematically illustrates a single arm of a medical device substantially similar to that illustrated in FIG. 3A, wherein the arm comprises surface features configured to enhance the ability of the arm to grip tissue;

FIG. 7A graphically illustrates the dependence of tissue sound velocity on temperature, indicating that there is a relative maximum at a temperature of approximately 50° C.;

FIG. 7B graphically illustrates a series of measured sound pulses that have been propagated through a sample of tissue as the temperature is increased, indicating that the temperature dependence illustrated in FIG. 6A is substantially duplicated in FIG. 6B;

Figure 3A:
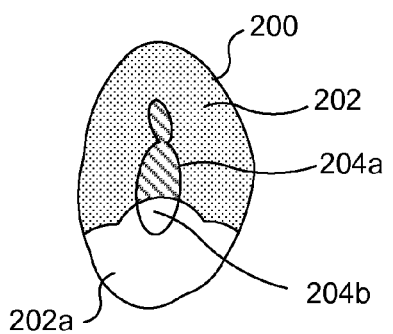
Figure 3A:
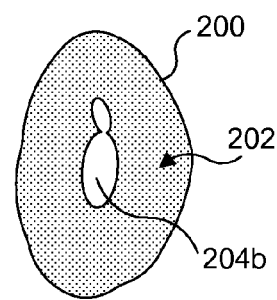
Figure 3A:
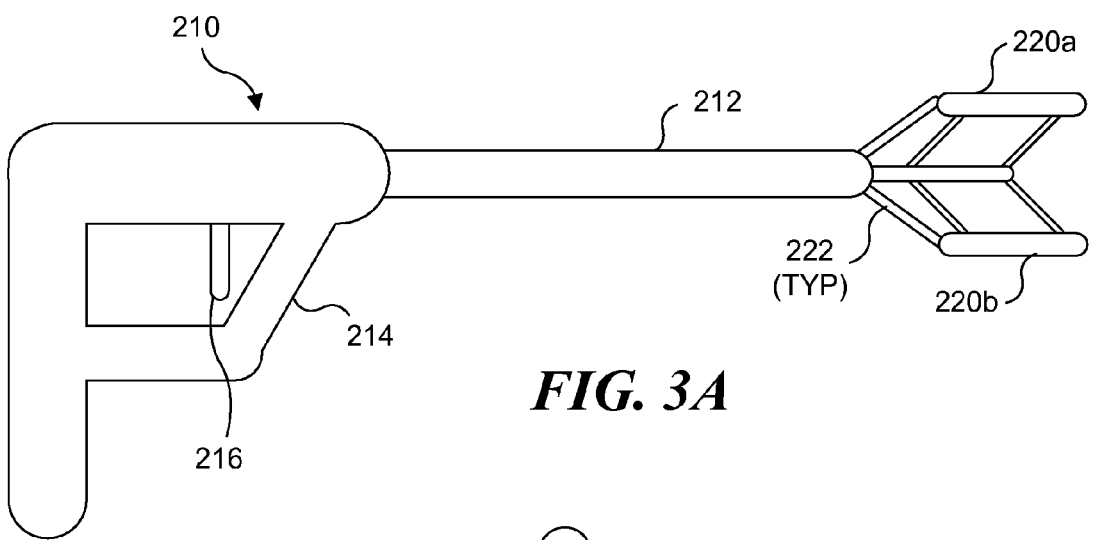

FIG. 10A schematically illustrates a heart and a left atrial appendage;

FIG. 10B schematically illustrates an exemplary medical device substantially similar to that illustrated in FIG. 3A being used to treat the left atrial appendage of FIG. 10A, in an exemplary procedure that substantially minimizes the risk of bleeding associated with treatment of the left atrial appendage; and FIG. 10C schematically illustrates a left atrial appendage including a substantially planar lesion (or necrotic/cauterized zone) after the treatment of FIG. 10B.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

In the description and claims that follow, it should be recognized that the term "therapeutic ultrasound" is intended to encompass high intensity ultrasound, both focused and unfocused. Those of ordinary skill in the art will readily recognized that such ultrasound is readily distinguishable from imaging ultrasound, which can be used to obtain an image of target tissue without affecting the target tissue. In contrast, therapeutic ultrasound imparts some therapeutic effect upon the tissue. In general, this therapeutic effect is tissue necrosis of undesired tissue. Tissue necrosis can be induced by therapeutic ultrasound by thermal and mechanical effects. Therapeutic ultrasound is often used to form a lesion of dead tissue. Depending on the configuration of the therapeutic ultrasound transducers, the lesion can be elliptical in shape, generally spherical in shape, or generally planar. Particularly preferred embodiments encompassed by the present disclosure rely on inducing a generally planar region of cauterized tissue using therapeutic ultrasound. Thus, the concepts disclosed herein can be implemented using a wide variety of different transducer designs, where the transducer can provide therapeutic levels of ultrasound (i.e., ultrasound that is more energetic than the ultrasound employed for imaging/diagnostic purposes). The therapeutic ultrasound can be unfocused, partially focused, or well focused. Curvature of the transducers can provide focusing when desired, or additional lens elements can be implemented to achieve focusing. Flat, generally unfocused transducers can also be implemented. In at least one embodiment, a substantially flat transducer array, which is not strongly focused and operates in the near-field is employed.

The disclosure provided herein describes apparatus and methods related to performing surgical procedures with a minimum of bleeding. Preferably, such procedures are minimally invasive procedures (such as laparoscopy, endoscopy, etc.); however, it should be recognized that the disclosed procedures and apparatus can also be applied to more invasive surgical procedures. The disclosed apparatus and methods can enable undesirable tissues, such as benign and malignant tumors, to be removed from the body without fear of uncontrolled bleeding that can result from such procedures using conventional techniques. Furthermore, during minimally invasive procedures that involve the removal of tissue, it is often necessary to apply Pringle maneuvers in which large blood vessels are clamped so that surgery can be performed without bleeding. The methods and apparatus described herein reduce or eliminate the requirement for clamping large blood vessels during surgery, thus preserving organs or other physiological structures from damage due to ischemia.

Figure 1A:
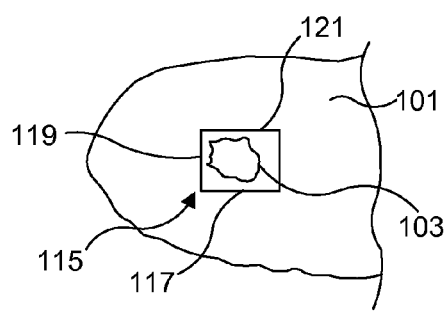
Figure 1B:
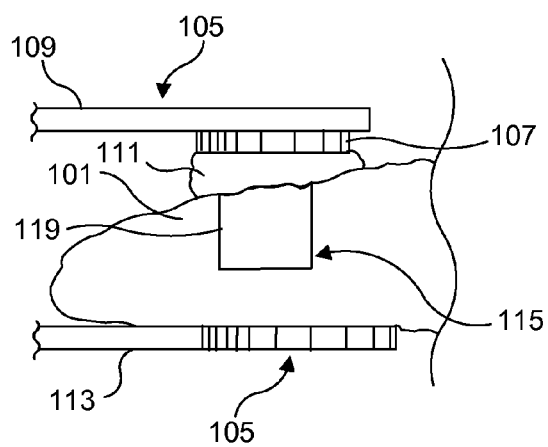

With respect to FIGS. 1A and 1B, a first embodiment of an exemplary apparatus 105 for performing cauterization to facilitate minimal blood loss surgery is shown. In FIG. 1A, there is shown a section of a liver 101, having a tumor 103. While such tumors are operable, because of the highly vascularized nature of the liver's pathological constitution (the average blood flow is about 25% of the resting cardiac output and the liver is a relatively soft organ that tears easily), liver surgery places the patient at substantial risk. Arresting a rapid liver hemorrhage (or even relatively slow bleeding) using conventional techniques is a time-consuming and difficult task.

FIG. 1B schematically illustrates apparatus 105, which includes an ultrasound transducer device 107 (configured to deliver therapeutic ultrasound) supported by a top arm 109, which is brought into contact with liver 101 by an acoustic coupler 111 (used to couple acoustic energy to the liver tissue). Coupler 111 comprises an acoustic-transmissive medium inside a flexible membrane. The membrane is highly elastic to enable it to conform to anatomical structures, is able to withstand the high ultrasonic intensities near the acoustic focus, is sufficiently tough to survive in a surgical environment, and is bio-compatible. It has been found that polyether polyurethane represents a particularly useful membrane material. Such a material is available commercially as PT9300 Dureflex™ polyurethane film, medical grade, 50 microns (0.002 inches) thick, and is available, for example, from Deerfield Urethane (South Deerfield, Mass.). Such a material is intended to be exemplary, rather than limiting, and other types of plastic films can instead be employed. It should be recognized that other types of acoustic couplers, such as relatively rigid water-filled cones, can also be beneficially employed. Furthermore, conventional coupling gels and fluids can be used in place of a non-amorphous acoustic coupler. It should further be recognized that some tissues may not require the use of an acoustic coupler, particularly where naturally occurring bodily fluids such as blood may provide the required coupling to the ultrasound transducer.

Referring once again to FIG. 1B, a bottom arm 113 slips under the tissue and aids in fixing a distance between transducer device 107 and tumor 103. Transducer device 107 is then activated and used to create a shell 115 of coagulated and necrotized tissue around tumor 103. In other words, prior to any surgical incision, the tumor is encapsulated by shell 115, such that tissue, which has been thoroughly cauterized using therapeutic ultrasound, substantially surrounds the tumor. The procedure for producing shell 115 is referred to as "presurgical volume cauterization," shell 115 comprising a volume of tissue approximately equal to the surface area times the thickness of the shell.

Changes in the appearance of cauterized planes 117, 119, and the like, of shell 115 are highly visible after the presurgical volume cauterization process. The tissue is essentially "cooked," that is; it is hardened and is warm to the touch. Shell 115 then provides a coagulated surgical pathway, so that surgical incisions can be made along the coagulated pathway, and little or no bleeding results. Note that, while in this exemplary embodiment, a box-shaped shell 115 has been formed in the liver tissue, depending upon the surgery to be performed, virtually any shape of necrosed tissue can be formed as needed, e.g., flat or planar, a curved surface, open or closed cubes and rectangles, inverted wedge shapes, inverted pyramids, open or closed cylinders, or the like, as would provide appropriate necrosed surgical pathways for the operation that will follow. The goal is to isolate a region of tissue from the blood supply that would otherwise be provided to it, by surrounding the surgical target with a necrosed surface. The particular shape of the surface chosen is selected to minimize the removal of viable non-diseased tissue as well as to make it a practical resection procedure for the surgeon.

Note that bottom arm 113 can incorporate an acoustic absorber on the distal side of the tissue from where the ultrasound energy is applied. The general purpose of the acoustic absorber is to absorb the ultrasound energy that passes through the tissue beyond the focal point, thereby insulating non-target tissues from being insonified. One desirable characteristic of such an absorber is its acoustic impedance (i.e., its density times the speed of sound) should ideally be equal to that of the tissue. With an absorber material having such a characteristic, most of the transmitted energy is absorbed, and there is little reflection of the energy impinging on the acoustic absorber back into the tissue. A second desired beneficial characteristic is that the absorber exhibit good acoustic absorbing properties at the frequency of the transducer emission, enabling acoustic energy to be absorbed rapidly by the acoustic absorber. A third desired beneficial characteristic is that the absorber material exhibit a thickness and thermal properties such that the surface of the acoustic absorber abutting the tissue does not become sufficiently hot to adversely affect the tissue.

Tan gum rubber has a lower impedance, approximately 1.5 Mrayls, but its loss is only about 4.3 dB/cm at 1.0 MHZ. This is the best material for use as the acoustic absorber known to date and, although requiring a thicker layer, aids in distributing heat caused by the energy it has absorbed and thus, avoids developing a hot surface. An alternative acoustically absorbent material is commercially available neoprene (available for example, from Gardico Inc., Seattle, Wash.), which has an impedance of 2.4 Mrayls, resulting in only about a five percent acoustic energy reflection. Red SBR rubber has similar loss characteristics, but has a higher impedance. However, red SBR rubber is adverse to wetting and any air layer disposed between the rubber and tissue will greatly increase the reflection coefficient. Hydrophobic materials, such as SBR rubber, should be wetted with alcohol before immersion to minimize such effects.

In an alternative exemplary embodiment, bottom arm 113 can incorporate an acoustically reflective material. If the coefficient of reflectivity is sufficiently high, little impinging energy will be transmitted to tissue or organs beyond, thus providing the benefit as achieved by using an acoustic absorber. The reflected energy can be used to enhance the procedure in the tissue of interest. A suitable reflector should have a characteristic acoustic impedance much different than that of the tissue, either lower (such as that of air or an air-filled material like Styrofoam™), or much higher (such as that of ceramics). For a low impedance reflector, a 180 degree phase reversal is produced at the point of reflection, which tends to cancel the effect of the impinging and reflected wave in the region proximate to the reflector. For a high impedance reflector, there is no phase reversal, so the impinging and reflected waves superimpose, producing an increased heating effect. Thus, a high impedance reflector might beneficially be disposed immediately adjacent to the target region. Furthermore, a mirror-reflection of a diverging beam impinging on the reflector is further diverging. Therefore, it is possible to obtain a broader area of effect in the region proximate to the reflector surface. If the focal point is closer to the transducer than the reflector, it is possible, by superposition, to produce effects with broader beams, beyond the maximum depth of focus.

Figure 2A:
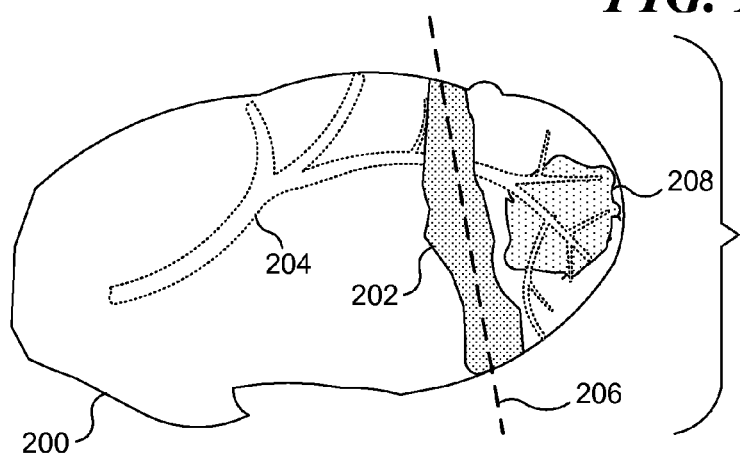
Figure 2B:
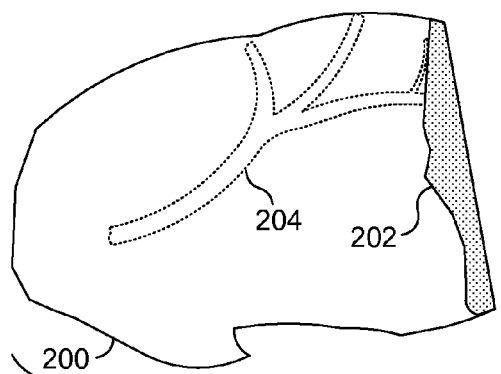
Figure 2B:
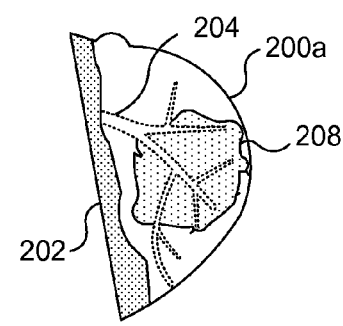

Referring to FIG. 2A, a kidney 200 includes vascular 204 and a tumor 208. It should be recognized that kidney 200 is schematically represented and that FIGS. 2A-2E are not intended to be anatomically correct. (In particular, an actual kidney would exhibit much more vascular structure than is represented in these Figures.) A generally planar portion 202 of kidney tissue has been treated with therapeutic ultrasound to cauterize or necrose a plane of the tissue. As indicated in FIG. 2B, an incision along planar portion 202 can be made with minimal bleeding, even though kidney tissue is highly vascularized, and bleeding is commonly associated with surgical procedures involving the kidney. Note that a tumor 208 is not part of planar portion 202. However, when an incision 206 is made along planar portion 202, kidney 200 is separated into a healthy portion 200a and a diseased portion 200b (which includes both healthy tissue and tumor 208). Planar portion 202 preferably exhibits substantially complete transmurality (i.e., the necrosed/cauterized tissue corresponding to planar portion 202 extends completely through the thickness of the kidney in all dimensions), and all blood vessels in planar portion 202 are preferably occluded. Under those conditions, diseased portion 202b can be excised with minimal (or no) bleeding.

Figure 2C:
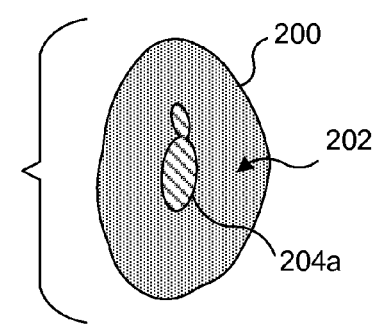

FIG. 2C schematically illustrates an end view of the kidney of FIG. 2B, indicating that the treated portion (i.e., planar portion 202) of the kidney exhibits complete transmurality, and all blood vessels 204a in the treated portion of the kidney are substantially occluded as desired. As noted above, the term "transmurality," as used herein and in the claims that follow, means that tissue is coagulated/necrosed all the way through from one end of the tissue mass to the opposing end of the tissue mass, without gaps. The cauterization may not be uniform, but the absence of gaps is important, because gaps will likely lead to undesired blood flow. Obtaining transmurality is a challenge, because lack of coagulation near blood vessels is problematical, since blood flow provides a cooling effect, reducing the effectiveness of the therapeutic ultrasound in causing occlusion of the blood vessels and tissue at those locations. Simply visually examining the exterior surface of the treated tissue will not provide an accurate indication as to whether such gaps exist within the mass of tissue. Thus, one major advantage provided by the exemplary method and apparatus disclosed herein is to enable a technique for empirically determining if transmurality has been achieved.

FIG. 2D schematically illustrates an end view of the kidney of FIG. 2B, indicating that the kidney has not been fully treated, such that the treated portion of the kidney (i.e., planar portion 202) does not exhibit complete transmurality, as indicated by non-coagulated portion 202a, and all blood vessels in the treated portion of the kidney are not substantially occluded, as indicated by non-occluded portion 204b, which is an undesirable result, since an incision into the treated (or untreated) tissue that pierces non-occluded portion 204b will result in bleeding.

FIG. 2E schematically illustrates an end view of the kidney of FIG. 2B, indicating that the kidney has not been fully treated, because although the treated portion of the kidney (i.e., planar portion 202) exhibits complete transmurality, not all blood vessels in the treated portion of the kidney are substantially occluded, as indicated by non-occluded portion 204b. Again, this result is undesirable, because an incision into the treated tissue that pierces non-occluded portion 204b will result in bleeding.

Significantly, exemplary apparatus 105 is not configured for introduction via a trocar (for use with minimally invasive surgery), nor is apparatus 105 configured to provide an indication of whether the target tissue is sufficiently treated (i.e., cauterized) to reduce or substantially eliminate blood loss. However, the present method and apparatus can provide the clinician an indication of whether the target tissue is sufficiently treated (i.e., cauterized) to reduce blood loss to an acceptable degree, and can be employed as a modified apparatus suitable for use with a trocar to facilitate minimally invasive procedures, with reduced blood loss. It should be recognized that the exemplary transducer disclosed above in connection with apparatus 105 can be implemented using transducers configured to generate either focused or unfocused high intensity ultrasound. Thus, the concepts disclosed herein can be implemented using transducers with minimal curvature (i.e., transducers incapable of generating a focused beam of high intensity ultrasound), as well as with transducers capable of providing high intensity ultrasound that is focused.

FIG. 3A schematically illustrates a laparoscopic clamp 210 that can be inserted through a trocar and into a body cavity, and once inserted, can expand such that opposed jaws of the clamp can engage relatively larger structures, such as a kidney. Clamp 210 includes a handle 214, and a trigger 216 (to enable the jaws of the clamp to be manipulated) disposed at a proximal end, an elongated shaft 212 (configured to be inserted through a trocar into a body cavity), and opposed jaws 220a and 220b at a distal end. Spreader bars 222 are coupled to the opposed jaws to initially enable the opposed jaws to be expanded after the clamp has been inserted into a body cavity, and later to enable the opposed jaws to be forced together to apply pressure on tissue disposed between the opposed jaws. It should be recognized that clamp 210 is intended to be exemplary, rather than limiting on the types of instruments that can be used, consistent with the present disclosure. Many other types of instruments having opposed jaws or arms upon which paired therapeutic transducers (or a therapeutic transducer paired with an acoustic reflector or acoustic absorber disposed on the opposing arm) can alternatively be used to implement the concepts disclosed herein. Medical clamps represent one type of instrument having such opposed jaws or arms and can be beneficially used to implement the concepts disclosed herein, particularly where it is desirable to apply pressure to the tissue being treated to collapse blood vessels in the tissue before treatment using therapeutic ultrasound. Medical retractors represent another type of instrument having such opposed jaws or arms that can be beneficially used to implement the concepts disclosed herein, if the clamping described above is not required. It should be recognized that many types of medical instruments having such opposed arms are known, and the concepts disclosed herein can be used to provide therapeutic ultrasound capability to such tools. While not specifically shown in FIG. 3A, clamp 210 can be configured to provide therapeutic ultrasound generally as described herein if a therapeutic transducer is disposed on jaw 220a, with an additional therapeutic transducer or an acoustic reflector (or acoustic absorber) being disposed on jaw 220b.

Figure 3B:
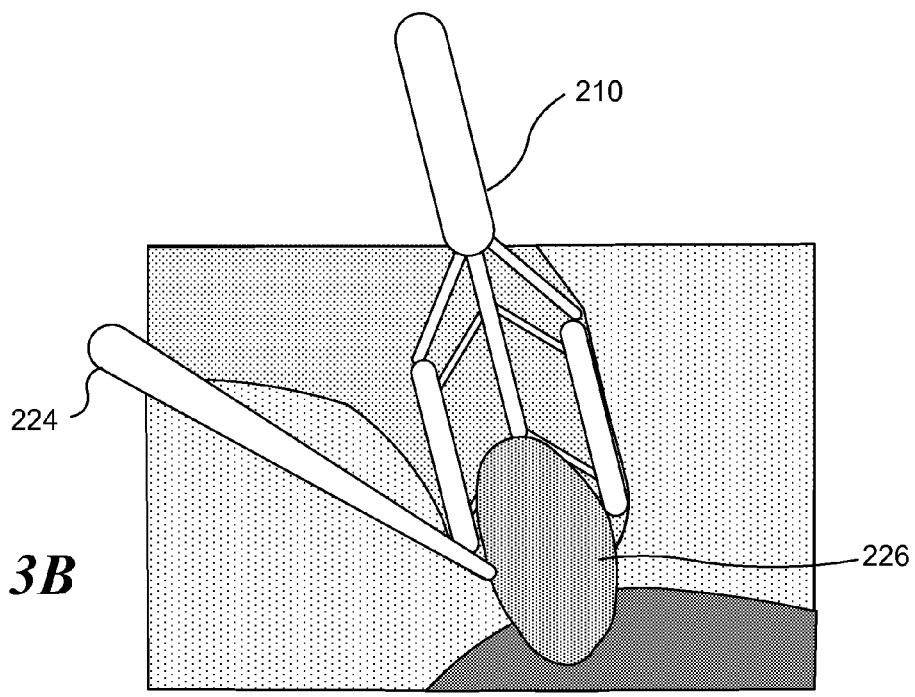

FIG. 3B schematically illustrates clamp 210 being positioned within an abdominal cavity and being used to clamp tissue 226. An additional laparoscopic tool 224 is also shown for reference purposes.

Figure 4:
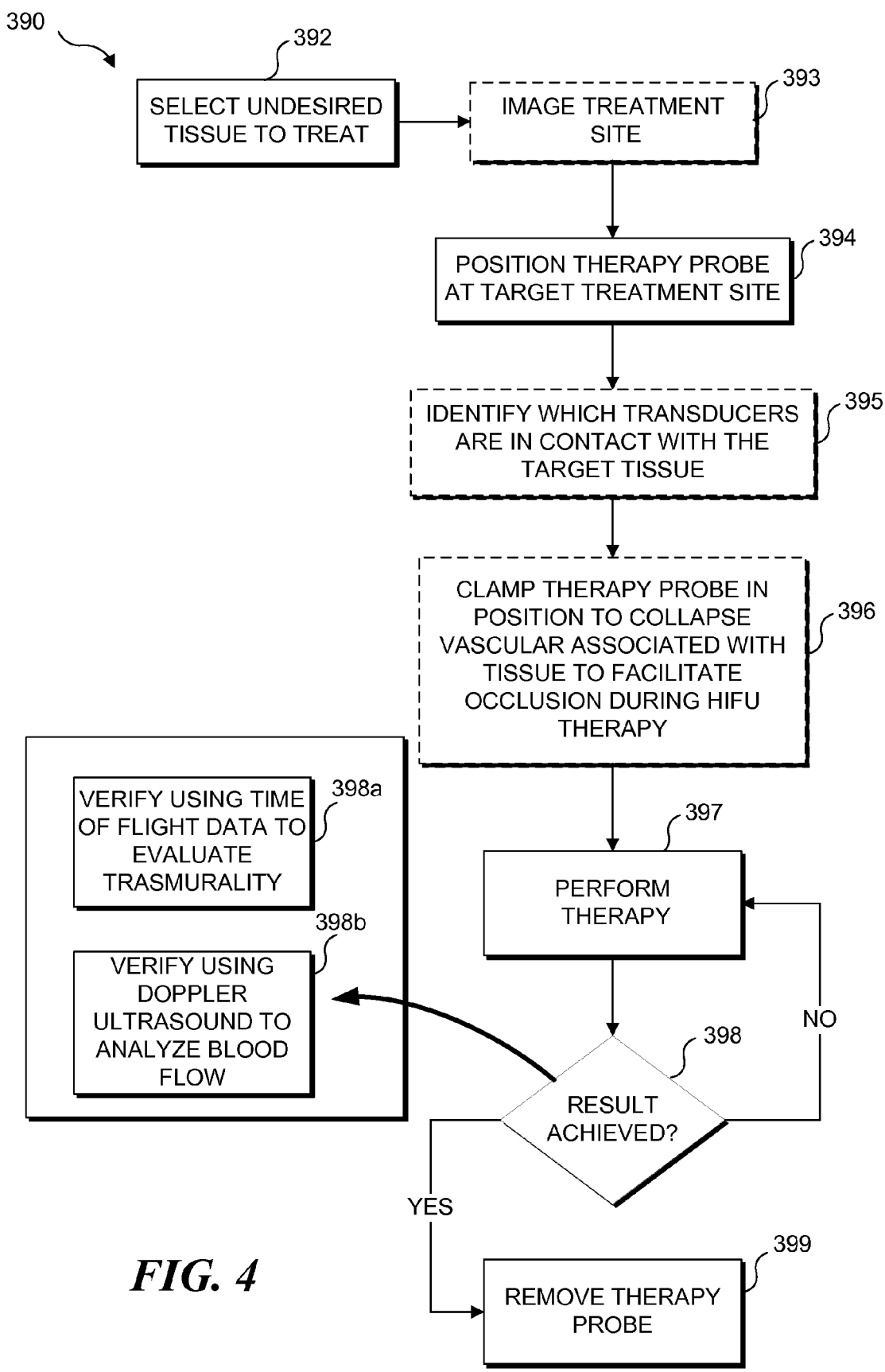

FIG. 4 is a flowchart 390 schematically illustrating exemplary steps of a method for using a medical device substantially similar to that illustrated in FIG. 3A, wherein at least one therapeutic transducer has been incorporated into at least one of the opposed arms. As described in greater detail below, various combinations of therapeutic transducers, therapeutic transducer arrays, acoustically reflective materials, and acoustically absorbent materials can be incorporated into the opposed arms. In order to provide a functional apparatus, at least one therapeutic transducer will need to be incorporated into at least one of the opposed arms. The other of the opposed arms can then incorporate either an acoustically reflective material, or at least one additional therapeutic transducer (or an acoustic absorber, generally as discussed above).

In a block 392, a specific region of tissue is selected for treatment. As noted above, the region of tissue to be treated can be part of an organ, part of a tumor, or part of a mass of tissue. Significantly, the tissue selected for treatment may not be diseased tissue (as shown in FIGS. 2A and 2B, a diseased portion may be disposed in a mass of tissue distal of the tissue being treated, such that the distal tissue can be removed with minimal bleeding; it should further be recognized that in some cases, the distal tissue may be completely separated from the vascular structure providing nutrients to the distal tissue, by the treated tissue, such that the distal tissue may be left in place to atrophy, rather than being removed).

Referring once again to FIG. 4, in an optional block 393, imaging of the treatment site is performed. Where the therapeutic ultrasound is being provided in a minimally invasive procedure, it will likely be desirable to image the treatment site and the position of the therapy probe (configured to provide the therapeutic ultrasound) relative to the treatment site, before initiating therapy. Where the therapeutic ultrasound is being provided in connection with an open surgical procedure, the clinician will likely be able to visualize the treatment site without requiring the imaging step. It should be recognized that such imaging can be implemented using techniques such as, but not limited to, imaging ultrasound, or magnetic resonance imaging (MRI). If desired, the imaging ultrasound transducers can be incorporated into the therapy probe, such that a single instrument can be used to provide both imaging ultrasound and therapeutic ultrasound (noting that some transducer designs enable the same transducer to be used for both imaging and therapy). In a block 394, the therapy probe is positioned proximate to the treatment site. It should be recognized that a therapy probe consistent with FIG. 1B or FIG. 3A can be used to implement this exemplary method.

In an optional block 395, the ultrasound transducers in the therapy probe are energized at a relatively low power to interrogate the target tissue (i.e., the ultrasound transducers are energized at a level insufficient to induce a therapeutic effect in the target tissue). This optional step can be used to determine if any of the transducers (or any elements in a transducer array) are not coupled with the target tissue. For example, depending on the size and shape of the region of tissue disposed between the opposed arms of the therapy probe, it is possible that some portion of an opposed arm including a transducer will not be acoustically coupled to the tissue. By determining which transducer or transducer elements in an array are not coupled to tissue, it is possible to prevent those transducers from being energized when other transducers or transducer elements are energized to provide therapeutic ultrasound. Only energizing transducer elements that are coupled to the target tissue will reduce the likelihood of therapeutic ultrasound being delivered to non-targeted tissue.

In an optional block 396, the therapy probe is clamped into position to collapse vascular associated with the tissue, to facilitate occlusion of blood flow during application of the therapeutic ultrasound. If clamping is desired, preferably a therapy probe consistent with FIG. 3A is used to implement the method (although it should be recognized that many different configurations of medical clamps can be modified to incorporate the transducers and other components discussed above, as required to provide the therapeutic ultrasound).

Once the therapy probe is properly positioned relative to the treatment site, in a block 397, the therapy transducers of the therapy probe are energized to provide therapeutic ultrasound generally as described above. It should be recognized that a duration of the therapy may be entirely under control of the clinician, or a duration of the therapy may be under the control of a processor configured to provide therapy for a predetermined period of time. In a decision block 398, the treated tissue is analyzed to determine if the desired result has been achieved. If so, the therapy probe is removed in a block 399. If not, additional therapy is provided, as indicated in block 397.

Where additional therapeutic ultrasound is required, the additional therapeutic ultrasound will generally be provided in relatively short durations. However, in at least one exemplary embodiment, the analysis of the treated tissue is performed at the same time the therapeutic ultrasound is being provided, such that application of the therapeutic ultrasound is not terminated until the analysis of block 398 indicates that the desired result has been achieved. Where application of the therapeutic ultrasound is under the direct control of the clinician, an audible, tactile, or visual indication can be provided to the clinician to indicate that the desired result has been achieved, so that the clinician can terminate the application of the therapeutic ultrasound. Where application of the therapeutic ultrasound is automatically controlled by a processor or computing device, the machine instruction controlling the automated process can be configured to automatically terminate the therapeutic ultrasound once the analysis of block 398 indicates that the desired result has been achieved.

The concepts disclosed herein encompass evaluating the treated tissue using at least one of two different techniques to determine if the desired result is achieved. Preferably, both techniques are implemented, although it should be recognized that in some embodiments only one of the two techniques is implemented to evaluate the treated tissue. A first technique to evaluate the treated tissue is indicated by a block 398a, where time-of-flight data is used to evaluate a transmurality of the treated tissue. FIGS. 2C and 2E are illustrative of the desired transmurality. The technique for evaluation transmurality, which are discussed in greater detail below in connection with FIGS. 7A and 7B, can monitor the temperature in the tissue sample in real-time. Particularly, where the vascular structure associated with the tissue is small (i.e., such as only a few small capillaries), substantially complete transmurality may correlate with substantially complete occlusion of the vascular flow. However, even where substantially complete transmurality has been achieved, each blood vessel in the treated tissue may not be substantially occluded, as generally indicated in FIG. 2E. Thus, it can be desirable to provide an additional technique to evaluate blood flow in the treated tissue. Such a technique is indicated in a block 398b, wherein Doppler ultrasound is used to analyze blood flow in the treated tissue. At least one Doppler ultrasound transducer can be included in at least one of the opposed arms of the therapy probe. It should be recognized, however, that the concepts disclosed herein also encompass an exemplary embodiment wherein a separate probe incorporating a Doppler ultrasound transducer is employed to analyze blood flow in the treated tissue. As noted above, one embodiment disclosed herein implements both techniques to verify that the treated tissue exhibits the desired transmurality, as well as substantial occlusion of blood flow in the treated tissue. However, it should be recognized that other embodiments encompassed by the present disclosure implement only evaluation of the transmurality of the treated tissue, or evaluation of blood flow in the treated tissue, but not both.

As noted above, a technique to evaluate blood flow in the treated tissue employs the Doppler capability of ultrasound. A previously developed portable Doppler-guided HIFU therapy system uses the same transducer for both the Doppler and HIFU modes, providing a seamless interface between detection and therapy (as taught by Yoo Y M, Zderic V., Managuli R., Vaezy S., and Kim Y., in an article entitled, "Real-time color Doppler imaging for HIFU therapy guidance," *Proceedings of the 5th International Symposium on Therapeutic Ultrasound*, G. ter Haar and I Rivens, eds., (AIP Press; New York, 2004), p. 36-39). This design incorporates sufficient flexibility to facilitate both intraoperative and transcutaneous procedures. In addition, the control system of this type of system is sufficiently versatile to facilitate use with nearly any single element HIFU transducer. However, the disclosed use of such a system is intended to be exemplary, rather than limiting in regard to the novel concepts disclosed herein.

The primary components of the combined HIFU/Doppler instrument include a custom designed signal generation/digitizing board, a custom designed power amplifier, a T/R (Transmit/Receive) switch, a single element HIFU transducer, and custom designed analog mixers. The MCU (micro processing unit) for the system is the Motorola Corporation type 68HC711E9™ microprocessor. The entire unit is sufficiently small to be packaged within a briefcase-size suitcase along with a controller, e.g., a Tablet computer. A software spectrum analyzer program is loaded onto the computer, providing a visual feedback for the quadrature "receive" signals, which are also coupled to a speaker system for providing an audio feedback signal, as well.

The transmit burst of this exemplary system is generated using an off-the-shelf oscillator and an Analog Devices type DDS (Direct Digital Synthesis) synthesizer chip (AD9850™), both located on the digitizer board. This chip is designed specifically to turn a clock source into a frequency programmable sine or square wave. The output of the synthesizer is then TTL (Transistor-Transistor Logic) gated to the desired number of transmit cycles. The gated output signal is input into a 100 Watt variable power amplifier, which is designed to provide a maximum of 200 V peak-to-peak transmit signal. The transmit signal output from the amplifier is then passed through a T/R switch, and supplied to drive the transducer.

The receive echoes return through the T/R switch, providing a return signal that is supplied through a series of amplifiers, to a custom-built analog mixer. This mixer uses the frequency signal generated from the two DDS chips on board the digitizer, which is programmed to run 90 degrees out of phase, to provide the I and Q (I=In phase; Q=Quadrature phase) reference signals. The quadrature (Doppler) output is then gated, and coupled through an audio jack to a speaker, and to the spectrum analyzer.

Figure 5A:
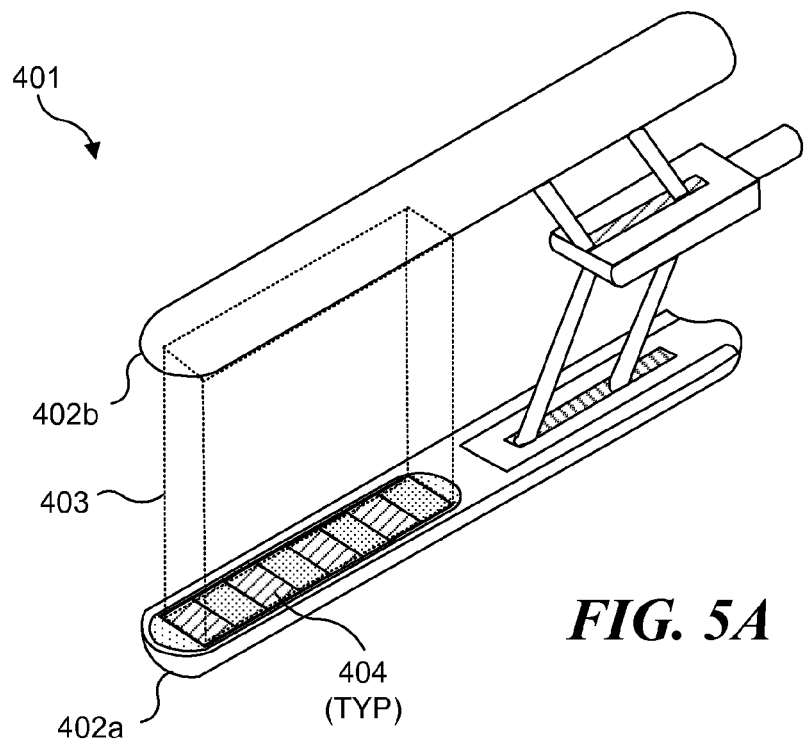

FIG. 5A schematically illustrates a plurality of therapy transducers combined with a surgical tool 401 including opposed arms 402a and 402b (generally similar to the clamp illustrated in FIG. 3A), such that a generally planar region of tissue 403 disposed between the opposed arms can be thermally treated using high intensity ultrasound to induce tissue necrosis. Arm 402a comprises an array of transducers 404 configured to provide therapeutic ultrasound. Arm 402b comprises a similar array of transducers, although as noted above, arm 402b can also incorporate an acoustically reflective material instead of the transducers. During treatment using therapeutic ultrasound, a high intensity ultrasound standing wave pattern is established in the generally planar region of tissue disposed between the opposed arms. While not specifically shown, it should be recognized that each arm incorporating a transducer can also incorporate electrical conductors configured to electrically couple the transducer to an external ultrasound machine to energize the transducer and/or to send data to the ultrasound machine.

Figure 5B:
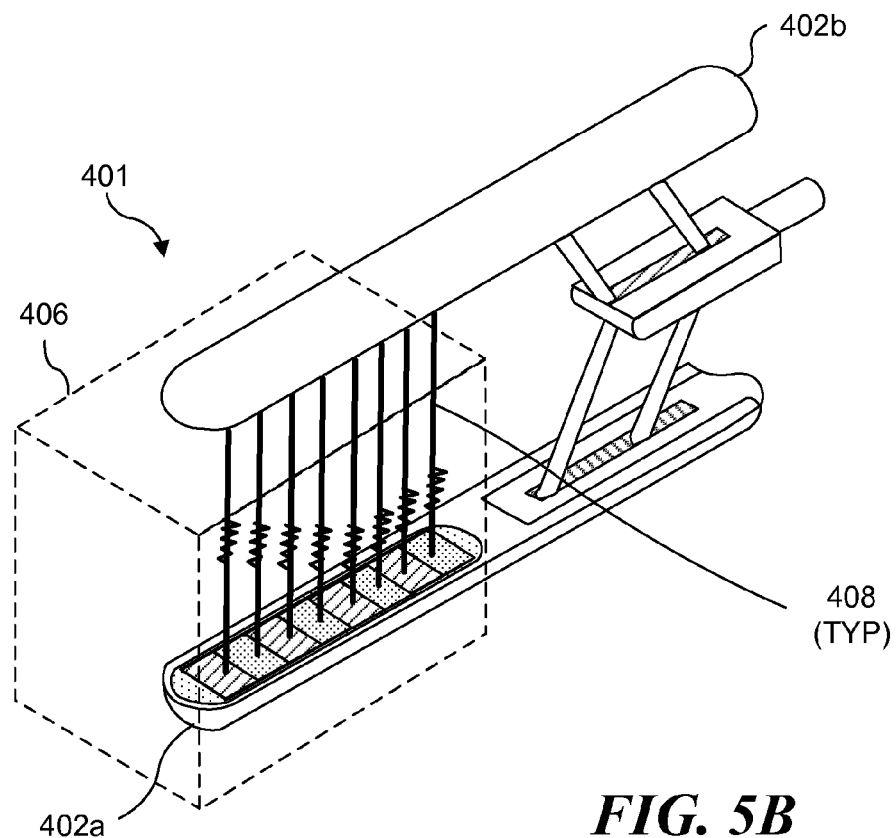

FIG. 5B schematically illustrates a technique for determining if a tissue sample 406 (at least that portion disposed between arms 402a and 402b) is completely cauterized with high intensity ultrasound (i.e., is completely transmural, or exhibits substantially complete transmurality), by using the time-of-flight of a number of ultrasound pulses 408, spread over the spatial extent of the tissue sample, to determine if the temperature in a particular tissue region has reached the cauterization temperature. As described in greater detail below, such a technique can be implemented where arm 402a comprises an array of therapeutic transducers (or a single transducer) to act as transmitters, and arm 402b comprises an array of transducers (or a single transducer) configured to act as receivers for the ultrasound pulses emitted by the ultrasound transducers in the array on arm 402a. A technique can also be implemented wherein arm 402a comprises an array of therapeutic transducers (or a single transducer), and wherein arm 402b comprises an acoustically reflective material configured to reflect the ultrasound pulses emitted by the ultrasound transducers in the array on arm 402a, back towards arm 402a, wherein at least some of the ultrasound transducers in the array on arm 402a then act as receivers to receive the reflected ultrasound pulses. As described in greater detail below, once such time-of-flight data have been collected, the data can be analyzed to determine if the desired transmurality has been achieved.

Figure 5C:
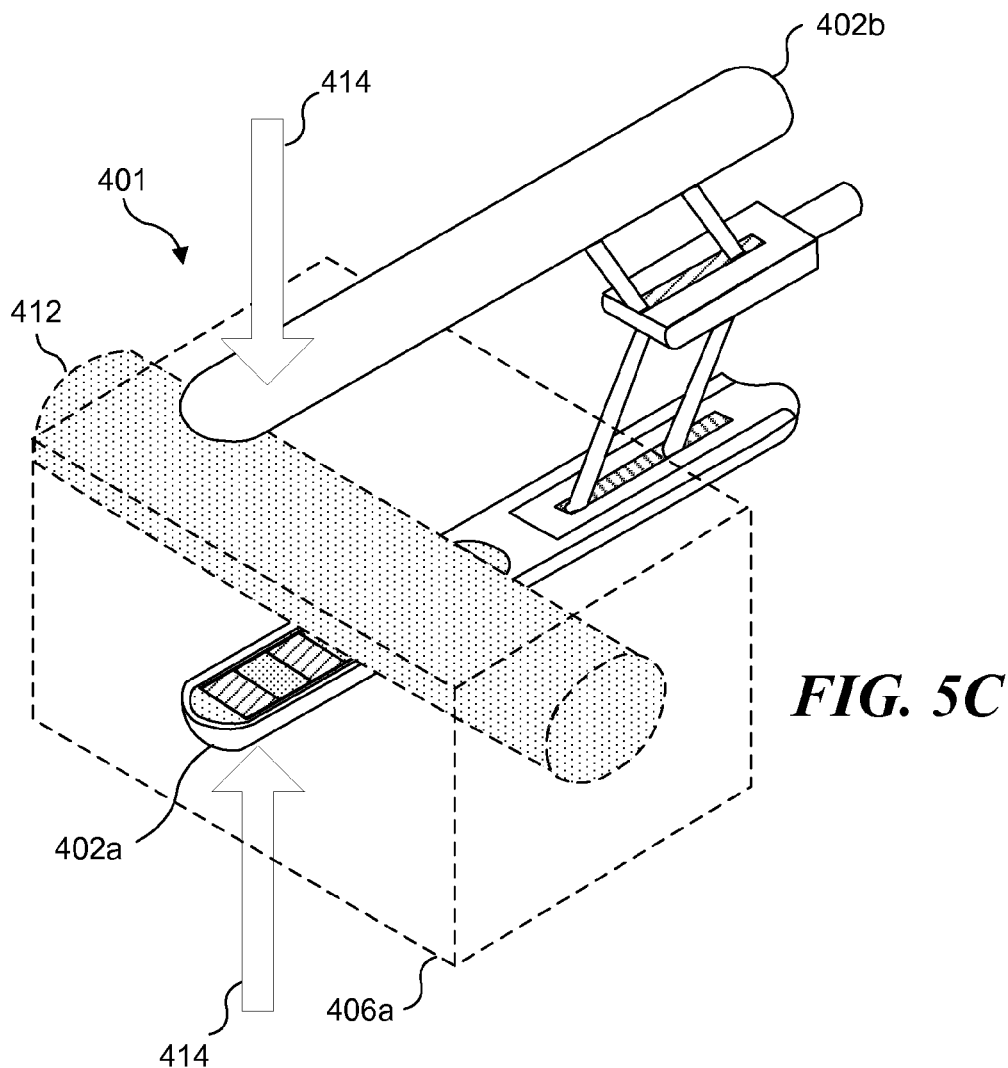

FIG. 5C schematically illustrates a plurality of therapy transducers combined with a surgical clamp such as illustrated in FIG. 3A, so that the opposed jaws of the clamp can squeeze tissue 406a to at least partially occlude blood vessels 412 in the tissue, before a generally planar region of tissue disposed between the opposed jaws of the clamp is thermally treated using high intensity ultrasound to induce tissue necrosis (i.e., cauterization). Clamping the tissue (i.e., exerting pressure on the tissue, as indicated by arrows 414) increases the likelihood that blood flow in the cauterized tissue will be substantially occluded.

Figure 6A:
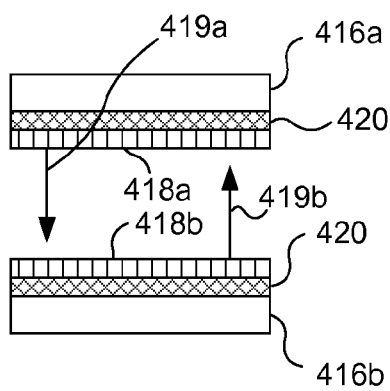

FIG. 6A schematically illustrates opposed arms of a medical device substantially similar to those illustrated in FIGS. 3A and 5A, wherein each opposed arm 416a and 416b comprises at least one ultrasound transducer 418a/418b, and an ultrasound absorbent material 420. As noted above, the layer of ultrasound absorbent material will prevent propagation of the therapeutic ultrasound beyond the generally planar region of tissue disposed between the opposed arms, thereby minimizing any tissue necrosis beyond the generally planar region of tissue. Therapeutic ultrasound waves 419a emitted from ultrasound transducer 418a are directed towards arm 416b, and are absorbed by the ultrasound absorbent material in arm 416b, so that therapeutic ultrasound waves 419a do not propagate beyond arm 416b. Similarly, therapeutic ultrasound waves 419b emitted from ultrasound transducer 418b are directed towards arm 416a, and are absorbed by the ultrasound absorbent material in arm 416a, so that therapeutic ultrasound waves 419b do not propagate beyond arm 416a. Ultrasound transducers acting as receivers in arm 416a can be configured to receive therapeutic ultrasound waves 419b from ultrasound transducer 418b, to generate the time-of-flight data as explained above. Similarly, ultrasound transducers acting as receivers in arm 416b can be configured to receive therapeutic ultrasound waves 419a from ultrasound transducer 418a, to generate the desired time-of-flight data.

It should be recognized that a further alternative would be to eliminate ultrasound transducer 418b, such that arm 416b includes absorbent material 420 but no transducer (substantially the configuration shown in FIG. 1B, which does not provide the transmurality feedback functionality). In such a configuration, absorbent material 420 in arm 416a is not needed.

Figure 6B:
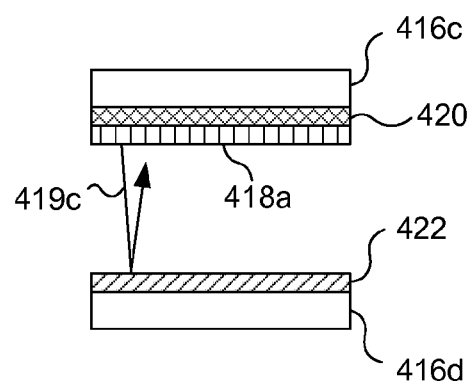

FIG. 6B schematically illustrates opposed arms of a medical device substantially similar to that illustrated in FIGS. 3A and 5A, wherein a first arm 416c comprises at least one ultrasound transducer 418a, and ultrasound absorbent material 420, and a second arm 416d comprises an ultrasound reflective material 422, such that therapeutic ultrasound waves 419c emitted by ultrasound transducer 418a are reflected back toward arm 416c. This reflection serves two purposes. First, it facilitates achieving transmurality of the tissue disposed between the two opposed arms. Second, reflected ultrasound waves can be received by transducers acting as receivers on arm 416c, to generate the time-of-flight data.

Figure 6C:
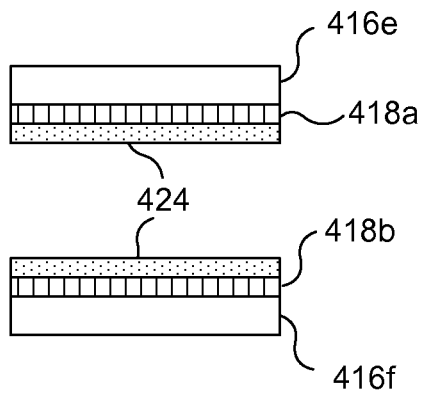

FIG. 6C schematically illustrates opposed arms of a medical device substantially similar to that illustrated in FIGS. 3A and 5A, wherein each opposed arm 416e and 416f comprises at least one ultrasound transducer 418a/418b, and a membrane 424 configured to facilitate acoustically coupling the at least one ultrasound transducer with tissue disposed between the opposed arms. It should be recognized that such a membrane can also be incorporated into the medical device of FIG. 6B (where the membrane is required on only one of the two opposed arms, i.e., the membrane is required only on the opposed arm incorporating the therapeutic ultrasound transducer, although it may be desirable to incorporate such a member to cover an acoustic reflector, to enhance coupling between the tissue and the acoustic reflector).

Figure 6D:
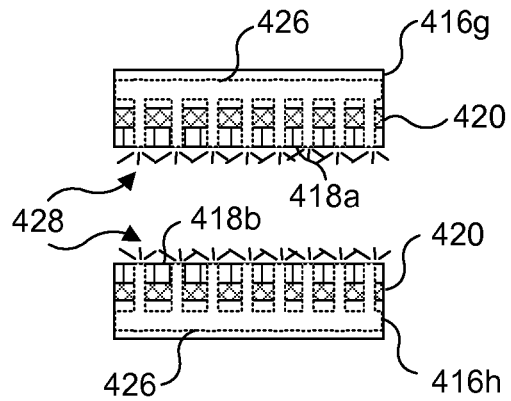

FIG. 6D schematically illustrates opposed arms of a medical device substantially similar to that illustrated in FIGS. 3A and 5A, wherein each opposed arm 416g and 416h comprises at least one ultrasound transducer 418a/418b, and a fluid conduit 426 configured to provide a coupling fluid/gel 428 to facilitate acoustically coupling the at least one ultrasound transducer with tissue disposed between the opposed arms. It should be recognized that such a fluid conduit can also be incorporated into the medical device of FIG. 6B (where the fluid conduit is required on only one of the two opposed arms, since the fluid conduit is required only on the opposed arm incorporating the therapeutic ultrasound transducer). It should be recognized that such a fluid conduit can be incorporated into one or both of the opposed arms of the medical device configured to provide therapeutic ultrasound in a variety of different ways, and the specific configuration shown in FIG. 6D is intended to be exemplary, rather than limiting. Instead of incorporating the fluid conduit within the body of the arm, generally as indicated in FIG. 6D, a separate fluid conduit, such as flexible tubing, could be used to provide the fluid conduit. Furthermore, where the medical device incorporates therapeutic transducers on only one of the opposed arms, the conduit need only be implemented on the arm including the ultrasound transducer. However, particularly in embodiments where the other opposed arm incorporates an acoustically reflective material, it may be desirable to also incorporate the fluid conduit on the other arm, to enhance an acoustic coupling between the arm comprising the acoustically reflective material and the target tissue.

Figure 6E:
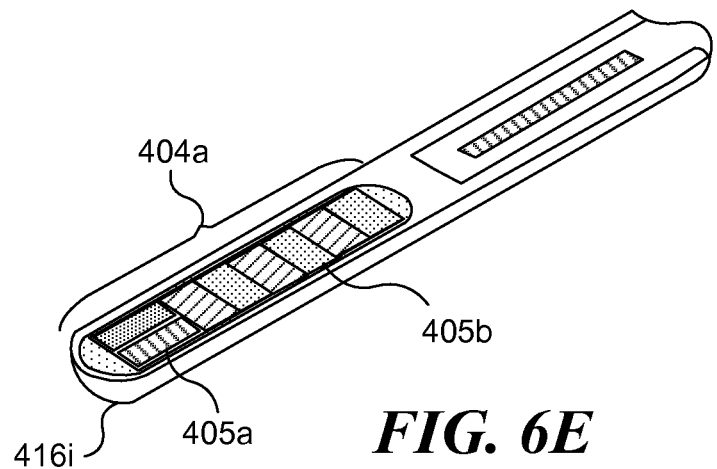

FIG. 6E schematically illustrates a single arm 416i of a medical device substantially similar to that illustrated in FIGS. 3A and 5A, wherein the arm comprises an ultrasound array including at least one element 405a disposed orthogonally to other elements 405b in the array. Having at least one element disposed along a different axis may enhance acquisition of data employed for Doppler ultrasound.

Figure 6F:
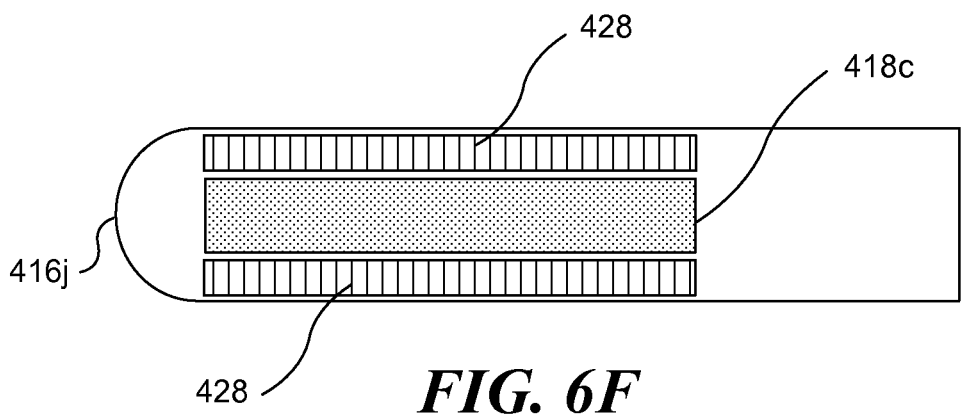

FIG. 6F schematically illustrates a single arm 416j of a medical device substantially similar to that illustrated in FIG. 3A, wherein the arm comprises a transducer 418c (or a transducer array) and surface features 428. The surface features are configured to enhance the ability of the arm to grip tissue. Such surface features can include any of ridges, serrations, bumps, grooves and other surface features that enhance the ability of the arm to grip tissue. In embodiments where such surface features are implemented, the surface features can be implemented on each of the two opposed arms in the device. It should be recognized that the orientation of the surface features relative to the transducer arm axes, as illustrated in FIG. 6F, is intended to be exemplary, rather than limiting. Those of ordinary skill in the art will readily recognize that the surface features can be implemented in many different configurations and orientations to enhance the gripping power of the arms. Furthermore, embodiments have been described herein where only one of two opposed arms incorporates transducers or transducer elements, and the other of the two opposed arms incorporates an acoustically reflective material or an acoustically absorbent material. Thus, it should be recognized that surface features can be implemented on arms that do not also include a transducer or transducer array.

With respect to materials that can be used to implement medical devices including opposed arms and transducers configured to provide therapeutic ultrasound, it should be recognized that the use of biocompatible materials can be important. Stainless steel and polymers represent exemplary biocompatible materials. Where an existing medical device such as a clamp or retractor has been retrofitted to incorporate the ability to provide therapeutic ultrasound, generally as described above, the materials used to retrofit the existing medical device can also be biocompatible. In general, such retrofit can be achieved by providing a kit including components intended to be attached to the opposed arms of the existing medical device. As discussed in detail above, at least one arm can be retrofitted to incorporate transducers configured to provide therapeutic ultrasound. The other opposed arm can be configured to incorporate similar transducers, acoustically absorbent materials, or acoustically reflective materials, generally as described above. Each such kit can be custom fabricated for a specific existing medical device, to ensure a precision fit, although a generic kit can alternatively be provided. The components in the kit can be attached to the existing medical device in a variety of ways, including the use of adhesives or by providing the kit components with a form factor enabling an interference fit of the components with the existing medical device to be achieved. It should be recognized that such attachment techniques are intended to be exemplary, rather than limiting.

Figure 7A:
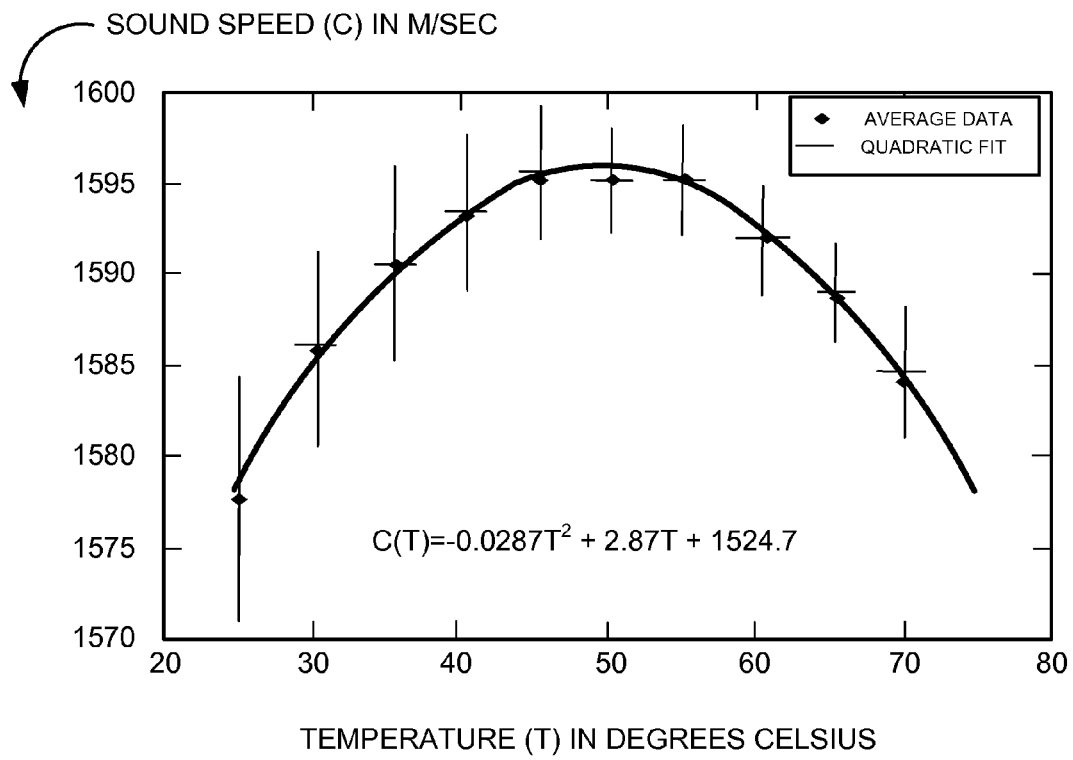
Figure 7B:
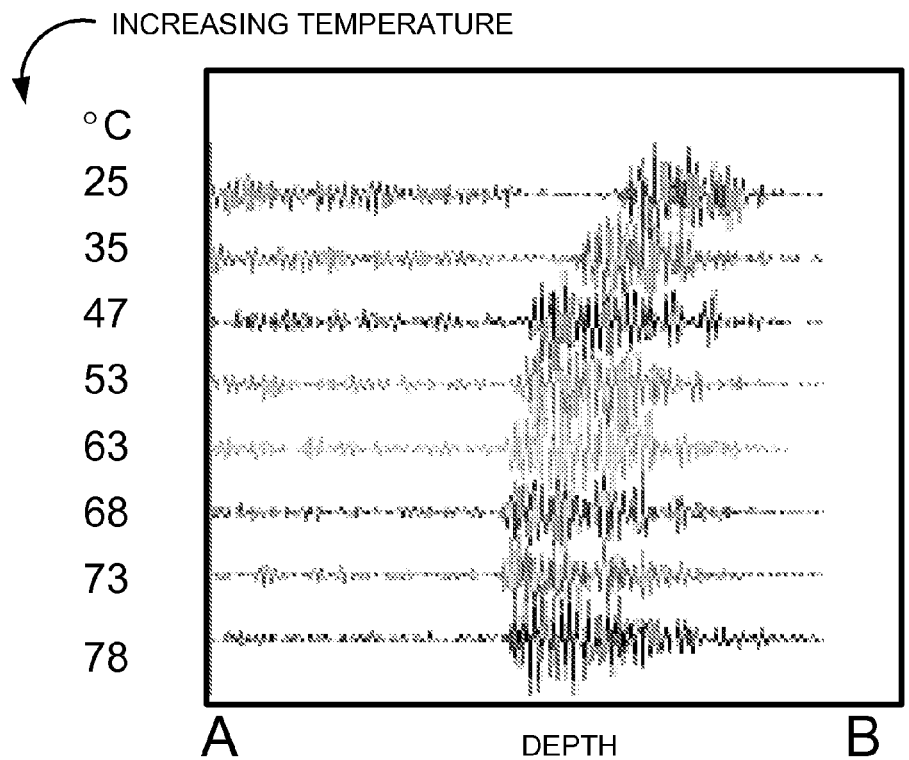

The tissue temperature monitoring and transmurality evaluation techniques noted above will now be described in greater detail. FIG. 7A graphically illustrates the dependence of tissue sound velocity on temperature; indicating that there is a relative maximum at a temperature of approximately 50° C. FIG. 7B graphically illustrates a series of measured sound pulses that have been propagated through a sample of tissue as the temperature is increased, indicating that the temperature dependence illustrated in FIG. 7A is substantially duplicated in FIG. 7B.

These techniques enable an empirical determination of the endpoint (i.e., whether the tissue or physiological structure has been sufficiently treated or cauterized to reduce blood loss) to be determined. A beneficial complement to endpoint determination is a real-time monitor of the progress of the therapy. A distinct advantage of ultrasound is its real-time imaging and therapy assessment capabilities. It is known that the velocity of sound in tissue is temperature dependent. An interesting aspect of this dependence is that the sound speed is double-valued—(see FIG. 7A). As the tissue temperature increases to approximately 50° C., protein de-naturization results in a positive-to-negative change in the slope of the sound velocity with temperature. Near 50° C., the slope is zero. This behavior has been observed in ex vivo tissue by observing the change in time-of-flight of a succession of sound pulses through a sample of this tissue as it was heated by high intensity ultrasound. Exemplary data are shown in FIG. 7B. Significantly, the time-of-flight of the ultrasound pulse replicates the behavior shown in FIG. 7A. This interesting result enables a determination of the transmurality of a high intensity ultrasound-induced lesion produced by a high intensity ultrasound device such as the one schematically illustrated in FIG. 5A (described in detail above). By transmitting an ultrasound pulse from a source transducer in one arm to a receiving transducer in the opposite arm of the device, the time-of-flight through the tissue contained between the arms can be measured. In one embodiment, pulses are transmitted from each of the (source) transducers in one arm and received by corresponding (receive) transducers in the other arm. In this manner, a series of time-of-flight displays can be generated, as graphically illustrated in FIG. 7B. If it is assumed that the tissue contained between the arms is heated uniformly by the high intensity ultrasound standing wave pattern (a reasonable assumption), then an observation that the time-of-flight passes through a minimum, and starts to increase indicates that the tissue is uniformly heated to and beyond the 50° C. denaturization temperature. Of course, it will be necessary to interleave the high intensity ultrasound and ultrasound monitoring pulses. Such interleaving/synchronization is described in U.S. Pat. No. 6,425,867, and is relatively simple to implement, particularly, since the time required to transmit and receive an interrogation pulse is less than a millisecond.

Figure 8:
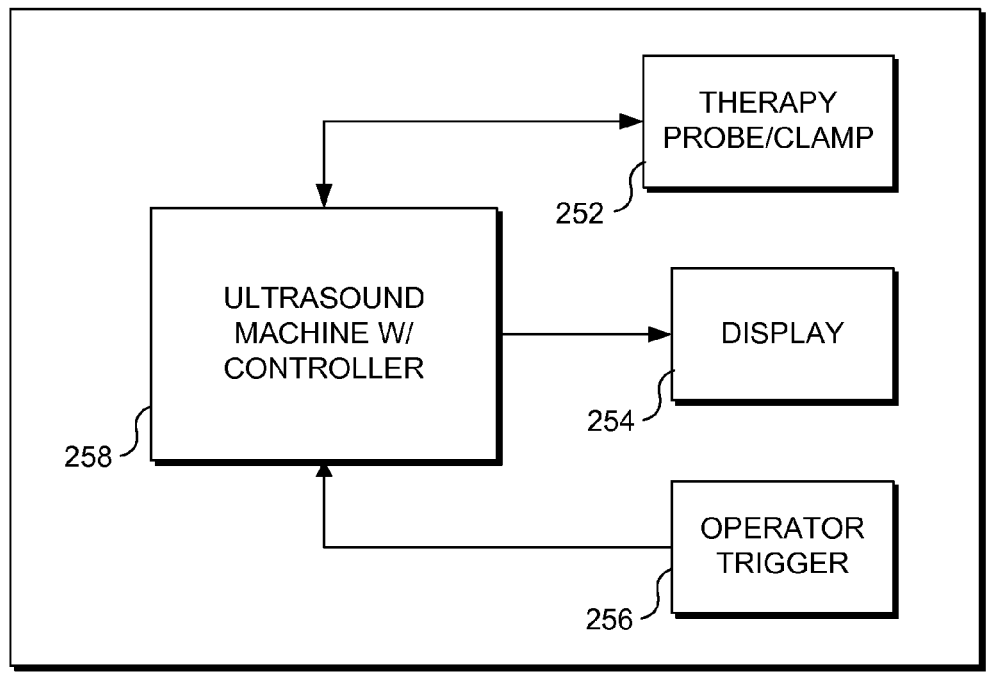
FIG. 8 is a block diagram schematically illustrating the basic elements in a system including a medical device substantially similar to that illustrated in FIG. 3A.

FIG. 8 is a block diagram schematically illustrating the basic elements of a system 250 that includes a medical device substantially similar to those illustrated in FIGS. 3A and 5A. System 250 includes a therapy probe/clamp 252 logically coupled with an ultrasound machine 258 (including a controller), a display 254 logically coupled with ultrasound machine 258, and a trigger 256 (enabling an operator to selectively energize the transducers in the therapy probe, or to engage a program stored in ultrasound machine 258 for controlling the therapy probe), also logically coupled to ultrasound machine 258. It should be recognized that therapy probe 252 can be configured for minimally invasive surgical techniques, or for open surgical techniques. Therapy probe 252 can incorporate a clamping mechanism configured to apply pressure to tissue disposed between opposed arms of the therapy probe, although it should be recognized that the present disclosure encompasses exemplary embodiments that do not incorporate such a clamping mechanism. It should also be recognized that therapy probe 252 can be a custom unit incorporating integrated therapeutic transducers (and/or acoustically reflective materials and/or acoustically absorbent materials, generally as discussed above with respect to FIGS. 6A-6E), or therapy probe 252 can be implemented using an existing medical tool comprising opposed arms (such as a retractor or a clamp) that has been modified by adding the therapeutic transducers to each arm (or at least one therapeutic transducer to one arm, with an acoustically reflective material added to the other arm). Where a duration of the therapeutic ultrasound transmission is under control of the clinician, the ultrasound machine is preferably configured to provide an indication to the clinician when a desired result has been achieved (based on analyzing the treated tissue for blood flow and/or transmurality, generally as described above). Such an indication can be audible (requiring the incorporation of speakers into system 250, not separately shown) or visual (for example, utilizing display 254 or an indicator light (not shown) logically coupled to ultrasound machine 258). Such an indication can also be tactile; for example, the therapy probe or operator trigger can incorporate a vibrating mechanism configured to be activated when the desired result has been achieved, to provide a haptic sensation that indicates to the clinician that the therapeutic ultrasound can be terminated. Where duration of the therapeutic ultrasound is under automated control of the ultrasound machine, the ultrasound machine (or its controlling software program) can be configured to terminate application of therapeutic ultrasound when a desired result has been achieved (based on analyzing the treated tissue for blood flow and/or transmurality, generally as described above).

In at least one exemplary embodiment, the ultrasound machine is configured to detect (using transducers acting as receivers in at least one of the opposed arms of the therapy probe) either cavitation or boiling (or both), and when such conditions are detected, to reduce power used to energize the transducers providing the therapeutic ultrasound.

Figure 9:
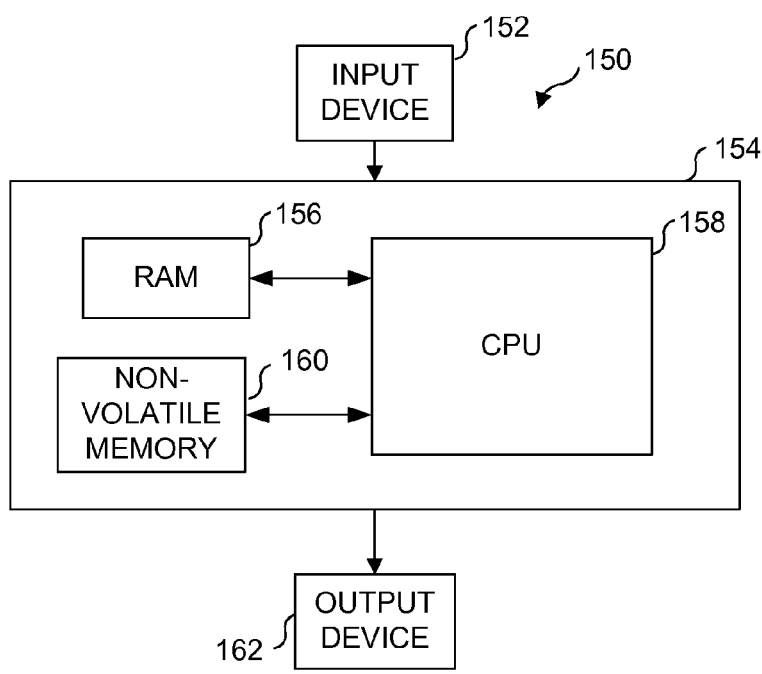
FIG. 9 is a block diagram schematically illustrating the basic elements in an exemplary computing device that can be beneficially incorporated into the system of FIG. 8.

FIG. 9 is a block diagram schematically illustrating the basic elements in a computing device that can be beneficially incorporated into the system of FIG. 8. It should be recognized that the controller incorporated into ultrasound machine 258 can be implemented as hardware (such as an application-specific integrated circuit or ASIC), although generally, any computing device having a processor and a memory in which machine language instructions are stored and executed by the processor for controlling the process can be employed. FIG. 9 and the following related discussion are intended to provide a brief, general description of a suitable computing environment, where the ultrasound machine incorporates a computing device.

Where a method or apparatus described herein requires means for evaluating transmurality, evaluating occlusion of blood vessels, evaluating whether a transducer is acoustically coupled to tissue, or determining if cavitation or boiling has been induced in a region of tissue treated with therapeutic ultrasound, it should be recognized that such means generally require processing and manipulation of ultrasound data, which can be implemented using hardware (generally as discussed above) or a computing device such as illustrated in FIG. 9. In general, the processor will be incorporated into an ultrasound machine used in conjunction with the therapy probe. In some cases, it would be possible to incorporate a processor into a therapy probe, however, such an embodiment would likely undesirably increase the cost of the therapy probe. As most ultrasound machines have processing capability, in general the required processing will be performed by the ultrasound machine. With respect to means for evaluating transmurality, the therapy probe will preferably incorporate at least one ultrasound transducer configured to act as a receiver, to provide the time-of-flight data to the processor for evaluating transmurality. A less desirable alternative would be to use a transducer incorporated into a separate probe to collect the time-of-flight data. With respect to means for evaluating occlusion of blood vessels, the therapy probe will preferably incorporate at least one ultrasound transducer configured to generate Doppler ultrasound data to be manipulated by the processor for evaluating occlusion of blood flow. A less desirable alternative would be to use a Doppler transducer incorporated into a separate probe to collect the Doppler ultrasound data. With respect to means for evaluating whether a transducer is acoustically coupled to tissue, the processor will be programmed to initially energize the ultrasound transducer at a relatively low or imaging power level, and to analyze reflected signal data to determine if the transducer is acoustically coupled to the tissue. Reflected signals from transducer elements acoustically coupled to tissue can be readily differentiated from reflected signals from transducer elements that are not acoustically coupled to tissue. With respect to means for determining if cavitation or boiling has been induced in a region of tissue treated with therapeutic ultrasound, the processor will be programmed to analyze reflected signal data for indications that cavitation or boiling is present in the region of tissue being treated by the therapeutic ultrasound. As described in detail above, techniques exist for interleaving imaging ultrasound with therapeutic ultrasound, and imaging ultrasound can be used to detect boiling or cavitation. Alternatively, other imaging modalities, such as MRI, can be used in place of ultrasound imaging to detect cavitation or boiling.

An exemplary computing system 150 suitable for incorporation into the ultrasound machine includes a processing unit 154 that is functionally coupled to an input device 152, and an output device 162, e.g., a display. Processing unit 154 includes a central processing unit (CPU 158) that executes machine instructions comprising a signal processing program for implementing the transmurality evaluation and/or blood flow and evaluation functions, as generally described above. In at least one exemplary embodiment, the machine instructions implement both functions, although as noted above, the present disclosure also encompasses exemplary embodiments in which only transmurality evaluation or only blood flow evaluation is performed. Additional signal processing can enable either an ultrasound image and/or a Doppler ultrasound image to be displayed to a user, as is generally known in the art. CPUs suitable for this purpose are available, for example, from Intel Corporation, AMD Corporation, Motorola Corporation, and from other sources.

Also included in processing unit 154 are a random access memory 156 (RAM) and non-volatile memory 160, which typically includes read only memory (ROM) and some form of memory storage, such as a hard drive, optical drive, floppy drive, etc. These memory devices are bi-directionally coupled to CPU 158. Such storage devices are well known in the art. Machine instructions and data are temporarily loaded into RAM 156 from non-volatile memory 160. Also stored in memory are the operating system software and ancillary software. While not separately shown, it will be understood that a generally conventional power supply will be included to provide the electrical power needed to energize computing system 150.

Input device 152 can be any device or mechanism that facilitates user input into the operating system, and into application programs running under the operating system, including, but not limited to, a mouse or other pointing device, a keyboard, a microphone, a modem, or other device to receive and respond to a user input. In general, the input device will be used to initially configure computing system 150, to achieve the desired signal processing, and for input of control decisions by the user. While not specifically shown in FIG. 9, it should be understood that computing system 150 is logically coupled to the therapy probe, display, and operator trigger of FIG. 8. Configuration of computing system 150 to achieve the desired signal processing includes the steps of loading appropriate signal processing software (i.e., machine executable instructions) into non-volatile memory 160, and launching the signal processing application (i.e., loading the signal processing software into RAM 156) so that the signal processing application is ready for use. Output device 162 generally includes any device that produces output information, but will most typically comprise a monitor or computer display designed for human visual perception of output. Accordingly, a conventional computer keyboard and computer display used in connection with the computing device should be considered as exemplary, rather than as limiting on the scope of this embodiment of the present disclosure. It should be recognized that at least one output provided by computing system 150 does not require a display, that output being either an audible, visual (i.e., activation of a light source as opposed to using the display to provide a visual indication), or tactile, generally as discussed above. Thus, in some exemplary embodiments, the display is not required in system 150. Such embodiments encompass those in which computing system 150 is specifically configured to terminate the therapeutic ultrasound when evaluation of the treated tissue (using either or both the transmurality evaluation and the blood flow evaluation discussed above) determines that additional treatment is not required, and those in which computing system 150 is specifically configured to provide at least one of an audible, visual, or tactile indication to the clinician, indicating that application of therapeutic ultrasound can be terminated.

While the concepts disclosed herein can be used to treat a wide variety of different tissues (including organ tissue and non-organ tissue), the partial nephrectomy of FIGS. 2A and 2B represent a particularly useful implementation, because conventional techniques for performing partial nephrectomies often lead to unacceptable blood loss. Yet another anatomical structure whose treatment according to conventional procedures is problematic is that of the left atrial appendage (LAA). Thus, another aspect of the concepts disclosed herein relates to treatment of the LAA during open chest cardiac surgery, or through a laparoscopic procedure, or during a thoracotomy. The LAA is believed to be a source of thrombus in the heart, leading to an increased risk of stroke. It is known that 90% of atrial fibrillation strokes are located in the LAA. Currently, the standard of care is to remove or occlude the LAA in current open heart cases to mitigate the risk of stroke and lower the need for anticoagulants. Current catheter ablation technologies do not offer surgeons the ability to remove the LAA in a minimally invasive procedure. Surveys indicate that physicians remove the LAA in more than 50% of such cases, with 31% removing it in all of their cases. Furthermore, it is known that there is a significant risk in tearing the LAA when traditional staples are used to exclude blood flow to the appendage. The devices and methods described above can thus be beneficially used to treat the LAA.

FIG. 10A schematically illustrates a heart 450, a LAA 452, and a distal end of a medical device 454 substantially similar to that illustrated in FIGS. 3A and 5A. FIG. 10B schematically illustrates medical device 454 being used to treat the LAA of FIG. 10A, in a procedure that substantially minimizes the risk of bleeding associated with treatment of the LAA (note that because of the orientation of medical device 454 in FIG. 10B, only one of the two arms can be seen in the Figure, the other arm being blocked from view by the first arm and the LAA). Device 454 comprises opposed arms 456a and 456b, configured to be clamped about the LAA using a force substantially sufficient to generally occlude blood flow in the LAA. At least one of the arms includes at least one therapeutic transducer configured to provide therapeutic ultrasound, generally as described above, to produce a generally planar lesion 458 between the opposed arms. FIG. 10C schematically illustrates generally planar lesion 458 having been formed in the LAA as a result of the application of therapeutic ultrasound. Note that FIGS. 10B and 10C are enlarged views of a portion 451 of FIG. 10A that includes the LAA. It should be recognized that device 454 can be implemented using any of the configurations disclosed in FIGS. 6A-6E.

An opening in the chest wall is made, generally in connection with a laparoscopic procedure or a thoracotomy. In cases of open chest surgery, the LAA would be exposed. Device 454 is used to clamp the LAA near the left atrium of the heart, excluding blood flow from the LAA. Once sufficient clamping pressure is applied and blood flow to the LAA is substantially occluded, the transducers (or at least one transducer) would be engaged to generate a generally planar region of tissue (i.e., lesion 458). Utilizing the feedback mechanisms described above to monitor blood flow and/or transmurality, the therapeutic ultrasound would be applied until a fully transmural region of tissue was obtained, and blood flow to the LAA was completed occluded. After determining that the blood flow was occluded, the clamp would be loosened, and a further check performed to verify that the blood flow in the LAA remains occluded. The apparatus can then be removed. If desired, the LAA can be removed by cutting along the necrotic zone. The LAA can often be left in place, to atrophy and be absorbed by normal biological processes.

It should be recognized that the therapy probes disclosed above with respect to FIG. 3A (in which the clamp incorporates the therapeutic transducers discussed above), FIGS. 5A-5C, and FIGS. 6A-6E are intended to be exemplary, rather than limiting. Many modifications can be made thereto to achieve high intensity ultrasound devices that can be used to facilitate surgical operations with minimal blood loss. Variations and combinations include the following: (1) high intensity ultrasound devices wherein the opposed arms are configured to exert sufficient clamping forces on tissue disposed between the opposed arms to collapse blood vessels walls so that they will be sealed by the application of the high intensity ultrasound, and the resulting thermal ablation and tissue cauterization that results; (2) high intensity ultrasound devices wherein ultrasound imaging transducers are incorporated into at least one of the opposed arms, to facilitate ultrasound imaging of adjacent physiological structures including the tissue disposed between the opposed arms; (3) high intensity ultrasound devices wherein a plurality of individual transducers are included in a single opposed arm; (4) high intensity ultrasound devices wherein a single transducer configured to emit high intensity ultrasound is included in a single opposed arm; (5) high intensity ultrasound devices wherein a single opposed arm includes at least one transducer configured to emit high intensity ultrasound and at least one transducer configured to act as a receiver; (6) high intensity ultrasound devices wherein each opposed arm includes at least one transducer configured to emit high intensity ultrasound; (7) high intensity ultrasound devices wherein a first opposed arm includes at least one transducer configured to emit high intensity ultrasound, while the other opposed arm includes a reflector configured to reflect high intensity ultrasound emitted from the first opposed arm; (8) high intensity ultrasound devices wherein at least one opposed arm includes at least one transducer configured to emit HIFU; (9) high intensity ultrasound devices wherein at least one opposed arm includes at least one transducer configured to emit high intensity ultrasound and wherein at least one opposed arm includes at least one transducer configured to act as a receiver to collect time-of-flight information; (10) high intensity ultrasound devices wherein each opposed arm includes at least one transducer configured to emit high intensity ultrasound and at least one transducer configured to act as a receiver to collect time-of-flight information; and, (11) high intensity ultrasound devices wherein at least one opposed arm includes at least one transducer configured to generate Doppler ultrasound data that can be used to determine blood flow conditions within tissue disposed between the opposed arms.

Additional details of devices including opposed arms that are configured to treat tissue disposed between the opposed arms to necrose or cauterize such tissue, to facilitate surgery with minimal blood loss are as follows. Again, it should be recognized that such embodiments are intended to be exemplary, rather than limiting.

A. High intensity ultrasound devices having a size enabling the apparatus to be used in connection with minimally invasive instruments, such as a laparoscope or endoscope that can be inserted through a trocar or similar entry device into the abdominal cavity, or other regions of the body. In cases for which an open surgery approach is available, a modified version of the devices described above, without the restrictions of size imposed by laparoscopy, can be used (see FIGS. 1A and 1B, modified such that send and receive transducers are disposed in arms 109 and 113, or modified to achieve one of the other exemplary embodiments described herein).

B. High intensity ultrasound devices including a pair of expandable parallel arms, of sufficient length to enclose the tissue under consideration, such as a kidney, a lobe of kidney, a benign or malignant tumor, an appendix, a LAA, or any other such tissues that are desired to be treated or removed from the body.

C. High intensity ultrasound devices including a pair of parallel arms, such that along each of the parallel arms is attached a single transducer, or an array of transducers, that can effectively radiate high intensity ultrasound in the frequency range of 1-15 MHz. In one configuration the acoustic waves emitted would be parallel self-focusing. In another configuration the acoustic waves would be focused via transducer shape or by using a focusing lens.

D. High intensity ultrasound devices including a pair of parallel arms incorporating water pillows or other coupling agents integrated into the device along the transducer face to insure proper acoustic coupling.

E. High intensity ultrasound devices including transducers connected to a power supply to drive the transducer through a cable that is enclosed in the center of the arm of the minimally invasive device. In this configuration, the power unit that supplies electrical energy to drive the transducers is located outside the body.

F. High intensity ultrasound devices configured to be used in minimally invasive procedures such that once the minimally invasive device was inserted into the abdominal cavity or other region of the body, the tissue of interest would be selected, the parallel arms of the apparatus expanded and these arms maneuvered so as to clamp adjacent to the portion of the tissue to be transected.

G. High intensity ultrasound devices including parallel arms configured to exert sufficient clamping strength to collapse blood vessels using the arms of the clamp, preventing blood flow to the region distal of the clamp.

H. High intensity ultrasound devices including at least one transducer configured to generate high intensity ultrasound sufficient to induce thermal ablation and tissue cauterization of the entire thickness of tissue contained within tissue disposed between opposed parallel arms. Blood vessels contained with the tissue would also be thermally ablated and the adjacent walls of the vessels fused together.

I. High intensity ultrasound devices including at least one transducer configured to receive time-of-flight of sound pulses to evaluate the transmurality of the lesion and to provide a real-time feedback to the user of successful completion of the procedure.

J. High intensity ultrasound devices including at least one transducer configured to interrogate the blood vessels contained within the arms of the device in a Doppler format to determine if blood flow still was present distal to the line of cauterization. If this interrogation indicated that blood flow still persisted, then additional high intensity ultrasound would be applied.

K. High intensity ultrasound devices configured to facilitate insertion of additional minimally invasive devices so that the tissues distal to the plane of cauterization could be removed without fear of bleeding.

L. High intensity ultrasound devices configured to reduce the requirement for additional surgery, since the tissue distal from the plane of cauterization would be devoid of blood supply and would then be absorbed by the body.

M. High intensity ultrasound devices configured to permanently occlude blood flow or block nerve signal transduction from locations disposed between parallel arms of the device.

N. High intensity ultrasound devices including opposed arms, at least one arm including one or more transducers configured to provide therapeutic ultrasound, each arm including at least one of the following elements: a transducer configured to provide therapeutic ultrasound, an acoustically reflective material, and an acoustically absorbent material.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. Apparatus for use during a medical procedure to isolate a first region of tissue from a blood supply, comprising:
   (a) a first arm on which is disposed at least one ultrasound transducer configured to treat a second region of tissue using therapeutic ultrasound, the second region of tissue being adjacent to and disposed between the first region of tissue and a source of blood for the first region of tissue; and
   (b) a second arm configured to be in a facing relationship with the first arm, with the second region of tissue to be treated positioned between the first arm and the second arm, the second arm comprising an additional ultrasound transducer;
   (c) the first and second arms configured to collect ultrasound pulse time-of-flight data for evaluation of the second region of tissue while the second region of tissue remains positioned between the first and second arms to determine an effectiveness of the therapeutic ultrasound treatment in occluding blood flow within the second region of tissue;
   (d) an ultrasound machine coupled with the one or more ultrasound transducers and configured to: receive the collected ultrasound pulse time-of-flight data, identify an increase in ultrasound time-of-flight through the second region of tissue during treatment, and, in response to identifying the increase in ultrasound time-of-flight through the second region of tissue, (1) indicate a need to cease treatment of the second region of tissue, or (2) automatically cease treatment of the second region of tissue.

2. The apparatus of claim 1, wherein the first and second arms are elongate.

3. The apparatus of claim 1, wherein the ultrasound machine provides feedback as to whether the second region of tissue has been sufficiently treated to prevent bleeding from a vascular structure in the first region of tissue that was treated, when the vasculature structure in the first region is coupled with a source of blood flow by a vasculature structure in the second region of tissue.

4. The apparatus of claim 3, wherein the ultrasound machine provides feedback indicative of whether blood flow in the second region of tissue that was treated has been occluded.

5. The apparatus of claim 1, wherein the ultrasound machine provides feedback as to whether blood flow in the first region of tissue has been occluded.

6. The apparatus of claim 1, further comprising a clamping mechanism configured to force the first and second arms against the second region of tissue, to at least partially occlude blood flow within the second region of tissue.

7. The apparatus of claim 1, wherein the first and second arms comprise opposing jaws of a medical clamp that has been modified to provide ultrasound therapy by disposing the at least one ultrasound transducer on at least one of the opposing jaws.

8. The apparatus of claim 7, wherein the medical clamp is configured for insertion into a body of a patient during a minimally invasive surgery.

9. The apparatus of claim 1, further comprising a fluid conduit configured to provide a coupling fluid to at least one of the first and second arms.

10. The apparatus of claim 1, wherein the at least one transducer of the first arm comprises an array of transducers.

11. The apparatus of claim 10, further comprising means for determining if each element in the array is acoustically coupled with the second region of tissue, such that only elements acoustically coupled with the second region of tissue are energized to transmit the therapeutic ultrasound.

12. The apparatus of claim 10, wherein at least one transducer element of the array is orthogonally disposed relative to other transducer elements of the array.

13. The apparatus of claim 1, wherein the first arm further comprises a biocompatible membrane configured to facilitate acoustically coupling the at least one ultrasound transducer to the second region of tissue.

14. The apparatus of claim 1, further comprising means for detecting either cavitation or boiling caused by the therapeutic ultrasound in the second region of tissue, and reducing a power level for energizing the at least one ultrasound transducer when either cavitation or boiling is detected so as to avoid further cavitation or boiling.

15. The apparatus of claim 1, wherein the first arm and second arm are fabricated from biocompatible materials.

16. The apparatus of claim 1, wherein the first arm and second arm are fabricated from sterilizable materials.

17. The apparatus of claim 1, further comprising means for focusing at least one transducer implemented on the apparatus.

18. A method for using therapeutic ultrasound to treat a region of tissue to occlude blood flow in the region of tissue, comprising the steps of:
   (a) selecting a region of tissue to be treated, the region of tissue comprising a first face and a second face, the second face being disposed opposite the first face, such that the region of tissue is disposed between the first and second faces;
   (b) positioning a first arm proximate the first face, the first arm comprising a therapeutic ultrasound transducer;
   (c) positioning a second arm proximate the second face, the second arm comprising an additional therapeutic ultrasound transducer;
   (d) energizing the therapeutic ultrasound transducer on the first arm to treat the region of tissue disposed between the first and second faces with therapeutic ultrasound for a period of time; and
   (e) collecting ultrasound pulse time-of-flight data;
   (f) evaluating the region of tissue using collected time-of-flight data while the region of tissue remains positioned between the first and second arms to determine if additional treatment with the therapeutic ultrasound is required to occlude blood flow in the region, wherein evaluating the region of tissue using collected time-of-flight data comprises identifying an increase in ultrasound time-of-flight through the region of tissue during treatment; and
   (g) in response to identifying the increase in ultrasound time-of-flight through the region of tissue, (1) indicating a need to cease treatment of the region of tissue or (2) automatically ceasing treatment of the region of tissue.

19. The method of claim 18, wherein the step of evaluating the region of tissue comprises the step of evaluating a transmurality of the region of tissue.

20. The method of claim 18, wherein the step of evaluating the region of tissue comprises the step of evaluating a blood flow within the region of tissue using Doppler ultrasound.

21. The method of claim 18, further comprising the step of providing feedback to a user indicative of whether additional therapeutic ultrasound treatment of the region of tissue is required to occlude blood flow through the region of tissue.

22. The method of claim 18, further comprising the step of applying pressure to the region of tissue with the first and second arms, to at least partially occlude blood flow through the region of tissue, before the step of energizing the at least one therapeutic ultrasound transducer to treat the region of tissue.

23. The method of claim 18, further comprising the step of coupling the first and second arms to opposed faces of a minimally invasive surgical tool.

24. The method of claim 18, wherein the first and second arms comprise elongate arms.

25. The method of claim 18, wherein the region of tissue comprises a left atrial appendage.

26. The method of claim 18, wherein the at least one transducer of the first arm comprises an array, further comprising the steps of:
(a) energizing each element of the array at a low power before applying therapeutic ultrasound, to determine if the element is acoustically coupled to the region of tissue; and
(b) then only energizing elements of the array that have been determined to be acoustically coupled to the region of tissue at a higher power, which is sufficient to provide the therapeutic ultrasound.

27. The method of claim 18, further comprising the step of monitoring the region of tissue for signs of either cavitation or a boiling caused by the therapeutic ultrasound, such that if either is detected, the step of energizing the at least one therapeutic ultrasound transducer to treat the region of tissue continues at a reduced power level so as to avoid further cavitation or boiling.

28. The apparatus of claim 18, wherein the region of tissue is planar.

29. The apparatus of claim 28, wherein the at least one ultrasound transducer of the first arm is configured to treat the region of tissue with therapeutic ultrasound to create a planar lesion.

30. A system for using therapeutic ultrasound to treat a region of tissue to occlude blood flow in the region of tissue and to provide an indication to an operator that the region of tissue has been sufficiently treated with the therapeutic ultrasound to occlude blood flow in the region, comprising:
(a) a therapy probe comprising a first arm including at least one ultrasound transducer configured to treat the region of tissue using the therapeutic ultrasound, and a second arm configured to be disposed in a facing relationship with the first member, such that the region of tissue to be treated extends between the first arm and the second member, the second arm comprising an additional ultrasound transducer that also produces the therapeutic ultrasound;
(b) an ultrasound machine coupled to the therapy probe, the ultrasound machine being configured to:
(i) drivingly control each ultrasound transducer in the therapy probe to treat the region of tissue using the therapeutic ultrasound; and
(ii) collect ultrasound pulse time-of-flight data;
(iii) evaluate the region of tissue using the collected time-of-flight data during or after a therapeutic ultrasound treatment has been rendered thereto and while the region of tissue remains between the first and second arms by identifying an increase in ultrasound time-of-flight through the region of tissue, and
(iv) in response to identifying the increase in ultrasound time-of-flight through the region of tissue, (1) indicate a need to cease treatment of the region of tissue or (2) automatically cease treatment of the region of tissue; and
(c) an output device coupled with the ultrasound machine, the output device configured to indicate to an operator when the region of tissue has been sufficiently treated with the therapeutic ultrasound to occlude blood flow through the region of tissue.

31. The system of claim 30, wherein the first and second arms comprise elongate arms.

32. The system of claim 30, wherein the output device comprises at least one element selected from the group consisting of:
(a) a speaker configured to provide an audible indication to the operator that the region of tissue has been sufficiently treated with the therapeutic ultrasound to occlude blood flow through the region of tissue;
(b) a light configured to provide a visual indication to the operator that the region of tissue has been sufficiently treated with the therapeutic ultrasound to occlude blood flow through the region of tissue; and
(c) a display that is configured to provide a visual indication to the operator that the region of tissue has been sufficiently treated with the therapeutic ultrasound to occlude blood flow through the region of tissue.

33. The system of claim 30, wherein the therapy probe further comprises a clamping mechanism configured to force the first and second arms against the region of tissue sufficiently to at least partially occlude blood flow within the region of tissue prior to rendering a treatment with the therapeutic ultrasound.

34. The system of claim 30, wherein the first and second arms of the therapy probe are configured to be coupled with opposing jaws of a medical clamp, to provide therapeutic ultrasound capability to such medical clamps.

35. The system of claim 30, wherein the at least one transducer of the first arm comprises an array of transducers, and wherein the ultrasound machine determines if each element in the array is acoustically coupled with the region of tissue and only energizes elements of the array that are acoustically coupled with the region of tissue to produce the therapeutic ultrasound.

36. The system of claim 30, wherein the ultrasound machine evaluates the region of tissue treated with the therapeutic ultrasound, by evaluating a transmurality of the region of tissue, wherein a determination by the ultrasound machine that transmurality has been achieved indicates that the region of tissue has been sufficiently treated with the therapeutic ultrasound.

37. The system of claim 36, wherein the therapy probe further comprises at least one transducer configured for Doppler ultrasound, and wherein the ultrasound machine evaluates the region of tissue after a treatment with the therapeutic ultrasound by using Doppler ultrasound to measure blood flow in the region of tissue, a occlusion of blood flow in the region of tissue indicating that the region of tissue has been sufficiently treated with the therapeutic ultrasound.

38. The system of claim 30, wherein the therapy probe further comprise at least one transducer configured for Doppler ultrasound, and wherein the ultrasound machine evaluates the region of tissue treated with the therapeutic ultrasound by using Doppler ultrasound to measure blood flow in the region of tissue, a occlusion of blood flow in the region of tissue indicating that the region of tissue has been sufficiently treated with the therapeutic ultrasound.

39. The system of claim 30, wherein the ultrasound machine automatically determines if cavitation or boiling has been induced in a region of tissue by the therapeutic ultrasound, and if so, reducing a power level it uses to energize each ultrasound transducer in the therapy probe to treat the region of tissue with the therapeutic ultrasound so as to avoid further cavitation or boiling.

40. The system of claim 30, wherein the ultrasound machine automatically:
  (a) energizes each ultrasound transducer in the therapy probe to provide a treatment with the therapeutic ultrasound for a predetermined period of time; and
  (b) evaluates the region of tissue to determine if an additional therapeutic ultrasound treatment is required, and if so, energizes each ultrasound transducer in the therapy probe to provide the additional therapeutic ultrasound treatment for an additional period of time, until a subsequent evaluation of the region of tissue indicates that further therapeutic ultrasound treatment is not required.

41. The system of claim 30, wherein the ultrasound machine automatically:
  (a) energizes each ultrasound transducer in the therapy probe to provide a treatment with the therapeutic ultrasound; and
  (b) simultaneously evaluates the region of tissue to determine if further therapeutic ultrasound treatment is required, such that when no further therapeutic ultrasound treatment is required, the energizing of each ultrasound transducer in the therapy probe is terminated.

42. A method for treating a left atrial appendage to occlude blood flow within at least a portion of the left atrial appendage, comprising the steps of:
  (a) positioning a first arm proximate a first portion of the left atrial appendage, the first arm comprising at least one therapeutic ultrasound transducer;
  (b) positioning a second arm proximate a second portion of the left atrial appendage, the second portion being opposite the first portion, such that a region of tissue is defined between the first and second portions of the left atrial appendage, the second arm comprising an additional therapeutic ultrasound transducer;
  (c) energizing the therapeutic ultrasound transducer on the first arm to treat the region of tissue disposed between the first and second arms for a period of time; and
  (d) collecting ultrasound pulse time-of-flight data;
  (f) evaluating the region of tissue using the collected time-of-flight data by monitoring for an increase in ultrasound time-of-flight through the region of tissue and applying an additional treatment with the therapeutic ultrasound so as to occlude blood flow in the region of tissue until the increase in ultrasound time-of-flight is identified.

43. The method of claim 42, wherein the step of evaluating the region of tissue comprises evaluating a blood flow within the region of tissue using Doppler ultrasound.

44. The method of claim 42, further comprising the step of applying pressure to the region of tissue with the first and second arms, to at least partially occlude a blood flow in the region of tissue, before the step of energizing each therapeutic ultrasound transducer to treat the region of tissue with the therapeutic ultrasound.

45. The method of claim 42, further comprising the step of coupling the first and second arms to opposed faces of a minimally invasive surgical tool, so that the tool is thus modified to provide the therapeutic ultrasound to the regions of tissue.

46. Apparatus for use during a medical procedure to isolate a first region of tissue from a blood supply, comprising:
  (a) a first arm on which is disposed at least one ultrasound transducer configured to treat a second region of tissue using therapeutic ultrasound, the second region of tissue being adjacent to and disposed between the first region of tissue and a source of blood for the first region of tissue; and
  (b) a second arm configured to be in a facing relationship with the first arm, with the second region of tissue to be treated positioned between the first arm and the second arm, the second arm comprising an acoustically absorbent material configured to absorb any residual therapeutic ultrasound transmitted from the at least one ultrasound transducer of the first arm after the therapeutic ultrasound has passed through the second region of tissue to reach the acoustically absorbent material, the acoustically absorbent material configured to inhibit the residual therapeutic ultrasound from adversely affecting tissue distally beyond the acoustically absorbent material; and
  (c) the first and second arms configured to collected ultrasound time-of-flight data for evaluation of the second region of tissue while the second region of tissue remains positioned between the first and second arm to determine an effectiveness of the therapeutic ultrasound treatment in occluding blood flow within the second region of tissue;
  (d) an ultrasound machine coupled with the one or more ultrasound transducers and configured to: receive the collected ultrasound pulse time-of-flight data, identify an increase in ultrasound time-of-flight through the second region of tissue during treatment, and, in response to identifying the increase in ultrasound time-of-flight through the second region of tissue, (1) indicate a need to cease treatment of the second region of tissue, or (2) automatically cease treatment of the second region of tissue.

47. Apparatus for use during a medical procedure to isolate a first region of tissue from a blood supply, comprising:
  (a) a first arm on which is disposed at least one ultrasound transducer configured to treat a second region of tissue using therapeutic ultrasound, the second region of tissue being adjacent to and disposed between the first region of tissue and a source of blood for the first region of tissue; and
  (b) a second arm configured to be in a facing relationship with the first arm, with the second region of tissue to be treated positioned between the first arm and the second arm, the second arm comprising an acoustically reflective material configured to reflect the therapeutic ultrasound that is transmitted from the at least one ultrasound transducer of the first arm that has passed through the second region of tissue to reach the acoustically reflective material, such that the therapeutic ultrasound reflected by the acoustically reflective material is directed back towards the first arm; and
  (c) the first and second arms configured to collected ultrasound time-of-flight data for evaluation of the second region of tissue while the second region of tissue remains positioned between the first and second arm to determine an effectiveness of the therapeutic ultrasound treatment in occluding blood flow within the second region of tissue;
  (d) an ultrasound machine coupled with the one or more ultrasound transducers and configured to: receive the collected ultrasound pulse time-of-flight data, identify an increase in ultrasound time-of-flight through the second region of tissue during treatment, and, in response to identifying the increase in ultrasound time-of-flight through the second region of tissue, (1) indicate a need to cease treatment of the second region of tissue, or (2) automatically cease treatment of the second region of tissue.

48. A method for using therapeutic ultrasound to treat a region of tissue to occlude blood flow in the region of tissue, comprising the steps of:
(a) selecting a region of tissue to be treated, the region of tissue comprising a first face and a second face, the second face being disposed opposite the first face, such that the region of tissue is disposed between the first and second faces;
(b) positioning a first arm proximate the first face, the first arm comprising a therapeutic ultrasound transducer;
(c) positioning a second arm proximate the second face, the second arm comprising an acoustically reflective material;
(d) energizing the therapeutic ultrasound transducer on the first arm to treat the region of tissue disposed between the first and second faces with therapeutic ultrasound for a period of time; and
(e) collecting ultrasound pulse time-of-flight data;
(f) evaluating the region of tissue using collected time-of-flight data while the region of tissue remains positioned between the first and second arms to determine if additional treatment with the therapeutic ultrasound is required to occlude blood flow in the region, wherein evaluating the region of tissue using collected time-of-flight data comprises identifying an increase in ultrasound time-of-flight through the region of tissue; and
(g) in response to identifying the increase in ultrasound time-of-flight through the region of tissue, (1) indicating a need to cease treatment of the region of tissue, or (2) automatically ceasing treatment of the region of tissue.

49. A method for using therapeutic ultrasound to treat a region of tissue to occlude blood flow in the region of tissue, comprising the steps of:
(a) selecting a region of tissue to be treated, the region of tissue comprising a first face and a second face, the second face being disposed opposite the first face, such that the region of tissue is disposed between the first and second faces;
(b) positioning a first arm proximate the first face, the first arm comprising a therapeutic ultrasound transducer;
(c) positioning a second arm proximate the second face, the second arm comprising an acoustically absorbent material;
(d) energizing the therapeutic ultrasound transducer on the first arm to treat the region of tissue disposed between the first and second faces with therapeutic ultrasound for a period of time; and
(e) collecting ultrasound pulse time-of-flight data;
(f) evaluating the region of tissue using the collected time-of-flight data while the region of tissue remains positioned between the first and second arms to determine if additional treatment with the therapeutic ultrasound is required to occlude blood flow in the region, wherein evaluating the region of tissue using collected time-of-flight data comprises identifying an increase in ultrasound time-of-flight through the region of tissue; and
(g) in response to identifying the increase in ultrasound time-of-flight through the region of tissue, (1) indicating a need to cease treatment of the region of tissue or (2) automatically ceasing treatment of the region of tissue.

50. A system for using therapeutic ultrasound to treat a region of tissue to occlude blood flow in the region of tissue and to provide an indication to an operator that the region of tissue has been sufficiently treated with the therapeutic ultrasound to occlude blood flow in the region, comprising:
(a) a therapy probe comprising a first arm including at least one ultrasound transducer configured to treat the region of tissue using the therapeutic ultrasound, and a second arm configured to be disposed in a facing relationship with the first arm, such that the region of tissue to be treated extends between the first arm and the second arm, the second arm comprising an acoustically absorbent material configured to absorb any residual therapeutic ultrasound transmitted from the at least one ultrasound transducer of the first arm, which has passed through the region of tissue to reach the acoustically absorbent material, the acoustically absorbent material configured to inhibit the residual therapeutic ultrasound from adversely affecting tissue distal of the acoustically absorbent material;
(b) an ultrasound machine coupled to the therapy probe, the ultrasound machine being configured to:
(i) drivingly control each ultrasound transducer in the therapy probe to treat the region of tissue using the therapeutic ultrasound; and
(ii) collect ultrasound pulse time-of-flight data;
(iii) evaluate the region of tissue using the collected time-of-flight data after a therapeutic ultrasound treatment has been rendered thereto and while the region of tissue remains between the first and second arms by identifying an increase in ultrasound time-of-flight through the region of tissue, to determine an effectiveness of the therapeutic ultrasound treatment in occluding blood flow within the region of tissue, and
(iv) in response to identifying the increase in ultrasound time-of-flight through the region of tissue, (1) indicate a need to cease treatment of the region of tissue or (2) automatically cease treatment of the region of tissue; and
(c) an output device coupled with the ultrasound machine, the output device configured to indicate to an operator when the region of tissue has been sufficiently treated with the therapeutic ultrasound to occlude blood flow through the region of tissue.

51. A system for using therapeutic ultrasound to treat a region of tissue to occlude blood flow in the region of tissue and to provide an indication to an operator that the region of tissue has been sufficiently treated with the therapeutic ultrasound to occlude blood flow in the region, comprising:
(a) a therapy probe comprising a first arm including at least one ultrasound transducer configured to treat the region of tissue using the therapeutic ultrasound, and a second arm configured to be disposed in a facing relationship with the first arm, such that the region of tissue to be treated extends between the first arm and the second arm, the second arm comprising an acoustically reflective material configured to reflect the therapeutic ultrasound transmitted from the at least one ultrasound transducer of the first arm, which has passed through the region of tissue to reach the acoustically reflective material, such that therapeutic ultrasound reflected by the acoustically reflective material is directed back towards the first arm;
(b) an ultrasound machine coupled to the therapy probe, the ultrasound machine being configured to:
(i) drivingly control each ultrasound transducer in the therapy probe to treat the region of tissue using the therapeutic ultrasound; and
(ii) collect ultrasound pulse time-of-flight data;

(iii) evaluate the region of tissue using the collected time-of-flight data after a therapeutic ultrasound treatment has been rendered thereto and while the region of tissue remains between the first and second arms by identifying an increase in ultrasound time-of-flight through the region of tissue, to determine an effectiveness of the therapeutic ultrasound treatment in occluding blood flow within the region of tissue, and (iv) in response to identifying the increase in ultrasound time-of-flight through the region of tissue, (1) indicate a need to cease treatment of the region of tissue or (2) automatically cease treatment of the region of tissue; and (c) an output device coupled with the ultrasound machine, the output device configured to indicate to an operator when the region of tissue has been sufficiently treated with the therapeutic ultrasound to occlude blood flow through the region of tissue.

52. A method for treating a left atrial appendage to occlude blood flow within at least a portion of the left atrial appendage, comprising the steps of:

(a) positioning a first arm proximate a first portion of the left atrial appendage, the first arm comprising at least one therapeutic ultrasound transducer;

(b) positioning a second arm proximate a second portion of the left atrial appendage, the second portion being opposite the first portion, such that a region of tissue is defined between the first and second portions of the left atrial appendage, the second arm comprising an acoustically reflective material;

(c) energizing the therapeutic ultrasound transducer on the first arm to treat the region of tissue disposed between the first and second arms for a period of time; and (d) collecting ultrasound pulse time-of-flight data;

(e) evaluating the region of tissue using the collected time-of-flight data by monitoring for an increase in ultrasound time-of-flight through the region of tissue and applying an additional treatment with the therapeutic ultrasound so as to occlude blood flow in the region of tissue until the increase in ultrasound time-of-flight is identified.

53. A method for treating a left atrial appendage to occlude blood flow within at least a portion of the left atrial appendage, comprising the steps of:

(a) positioning a first arm proximate a first portion of the left atrial appendage, the first arm comprising at least one therapeutic ultrasound transducer;

(b) positioning a second arm proximate a second portion of the left atrial appendage, the second portion being opposite the first portion, such that a region of tissue is defined between the first and second portions of the left atrial appendage, the second arm comprising an acoustically absorbent material;

(c) energizing the therapeutic ultrasound transducer on the first arm to treat the region of tissue disposed between the first and second arms for a period of time; and (d) collecting ultrasound pulse time-of-flight data;

(e) evaluating the region of tissue with the collected time-of-flight data by monitoring for an increase in ultrasound time-of-flight through the region of tissue and applying an additional treatment with the therapeutic ultrasound so as to occlude blood flow in the region of tissue until the increase in ultrasound time-of-flight is identified in response.

* * * * *